US012657654B2

(12) United States Patent
Gong et al.

(10) Patent No.: US 12,657,654 B2
(45) Date of Patent: Jun. 16, 2026

(54) DUAL-SCREEN ASSISTIVE DISPLAY METHODS AND DEVICES SUITABLE FOR PEOPLE WITH LOW VISION AND APPARATUSES

(71) Applicant: HANGZHOU DUKANG TECHNOLOGY CO., LTD., Hangzhou (CN)

(72) Inventors: Zezhi Gong, Hangzhou (CN); Xiang Ying, Hangzhou (CN); Xinwei Huang, Hangzhou (CN)

(73) Assignee: HANGZHOU DUKANG TECHNOLOGY CO., LTD., Hangzhou (CN)

( * ) Notice: Subject to any disclaimer, the term of this patent is extended or adjusted under 35 U.S.C. 154(b) by 108 days.

(21) Appl. No.: 19/192,566

(22) Filed: Apr. 29, 2025

(65) Prior Publication Data

US 2025/0336031 A1 Oct. 30, 2025

(30) Foreign Application Priority Data

Apr. 29, 2024 (CN) .......................... 202410525591.8

(51) Int. Cl.
*G06T 3/40* (2024.01)
*G06F 3/14* (2006.01)
*G16H 30/40* (2018.01)

(52) U.S. Cl.
CPC .................. *G06T 3/40* (2013.01); *G06F 3/14* (2013.01); *G16H 30/40* (2018.01)

(58) Field of Classification Search
CPC ................... G06F 3/04842; G06F 3/14; G06F 2203/04805; G06F 3/04845; G06T 3/40; G16H 30/40
See application file for complete search history.

(56) References Cited

U.S. PATENT DOCUMENTS 7,694,234 B2 * 4/2010 Fleisher ................ G06F 3/0481
715/801
7,712,046 B2 * 5/2010 Ngari ........................ G06F 3/14
715/800
(Continued)

FOREIGN PATENT DOCUMENTS

CN 101188104 A 5/2008
CN 101685618 A 3/2010
(Continued)

OTHER PUBLICATIONS

Machine translation obtained from Google Patents of WO2013139089A1 (Year: 2013).*
(Continued)

*Primary Examiner* — Courtney Joan Nelson
(74) *Attorney, Agent, or Firm* — PORUS IP LLC

(57) ABSTRACT

Disclosed is a dual-screen assistive display method and device for people with low vision and an apparatus. The method comprises: determining position information of microscopic region virtual frame referenced to a display image on a primary screen based on a zoomLevel selected by a user; mapping the position information of the microscopic region virtual frame to position information of a microscopic highlight frame within a primary screen coordinate system; scanning a movement state of the microscopic highlight frame within the primary screen coordinate system to obtain starting coordinates of the microscopic highlight frame after movement; performing reverse mapping on the starting coordinates of the microscopic highlight frame after movement to obtain starting coordinates of the microscopic region virtual frame after movement; extracting an image content within the microscopic region virtual frame; microscopically magnifying an extracted image con-
(Continued)

Determining position information of a microscopic region virtual frame referenced to a display image on a primary screen based on a zoomLevel selected by a user, the zoomLevel being a current microscopic control magnification level, the position information including starting coordinates and dimensions of the microscopic region virtual frame
S101

Mapping, based on a display parameter of the primary screen and a resolution of the display image on the primary screen, the position information of the microscopic region virtual frame to position information of a microscopic highlight frame within a primary screen coordinate system
S102

Scanning a movement state of the microscopic highlight frame within the primary screen coordinate system to obtain starting coordinates of the microscopic highlight frame after movement
S103

Performing reverse mapping on the starting coordinates of the microscopic highlight frame after movement to obtain starting coordinates of the microscopic region virtual frame after movement.
S104

Extracting an image content within the microscopic region virtual frame based on the dimensions and the starting coordinates of the microscopic region virtual frame after movement
S105

Microscopically magnifying an extracted image content within the microscopic region virtual frame on a secondary screen
S106 tent within the microscopic region virtual frame on a secondary screen.

20 Claims, 9 Drawing Sheets

(56)                    References Cited

U.S. PATENT DOCUMENTS

| | | | | |
|---|---|---|---|---|
| 10,324,532 | B2 * | 6/2019 | Le Rouzo | G09B 21/005 |
| 2012/0200724 | A1 * | 8/2012 | Dua | H04N 23/69 |
| | | | | 348/222.1 |
| 2014/0368627 | A1 * | 12/2014 | Kalvenes | G02B 27/027 |
| | | | | 348/63 |
| 2015/0110456 | A1 * | 4/2015 | Yoon | H04N 23/661 |
| | | | | 386/224 |
| 2021/0117048 | A1 * | 4/2021 | Grieves | G06F 3/01 |

FOREIGN PATENT DOCUMENTS

| | | | | |
|---|---|---|---|---|
| CN | 102662566 | A | 9/2012 | |
| CN | 103049135 | A | 4/2013 | |
| CN | 103049136 | A | 4/2013 | |
| CN | 105812778 | A | 7/2016 | |
| CN | 106201252 | A | 12/2016 | |
| CN | 106293390 | A | 1/2017 | |
| CN | 109828710 | A | 5/2019 | |
| CN | 111784615 | A | 10/2020 | |
| CN | 114666427 | A | 6/2022 | |
| CN | 115758502 | A | 3/2023 | |
| KR | 20100081821 | A | 7/2010 | |
| KR | 102613415 | B1 | 12/2023 | |
| WO | WO-2013139089 | A1 * | 9/2013 | G06F 3/0484 |
| WO | 2014186972 | A1 | 11/2014 | |

OTHER PUBLICATIONS

First Office Action in Chinese Application No. 202410525591.8 mailed on Jun. 4, 2024, 11 pages.
Notification to Grant Patent Right for Invention in Chinese Application No. 202410525591.8 mailed on Jun. 17, 2024, 4 pages.

* cited by examiner

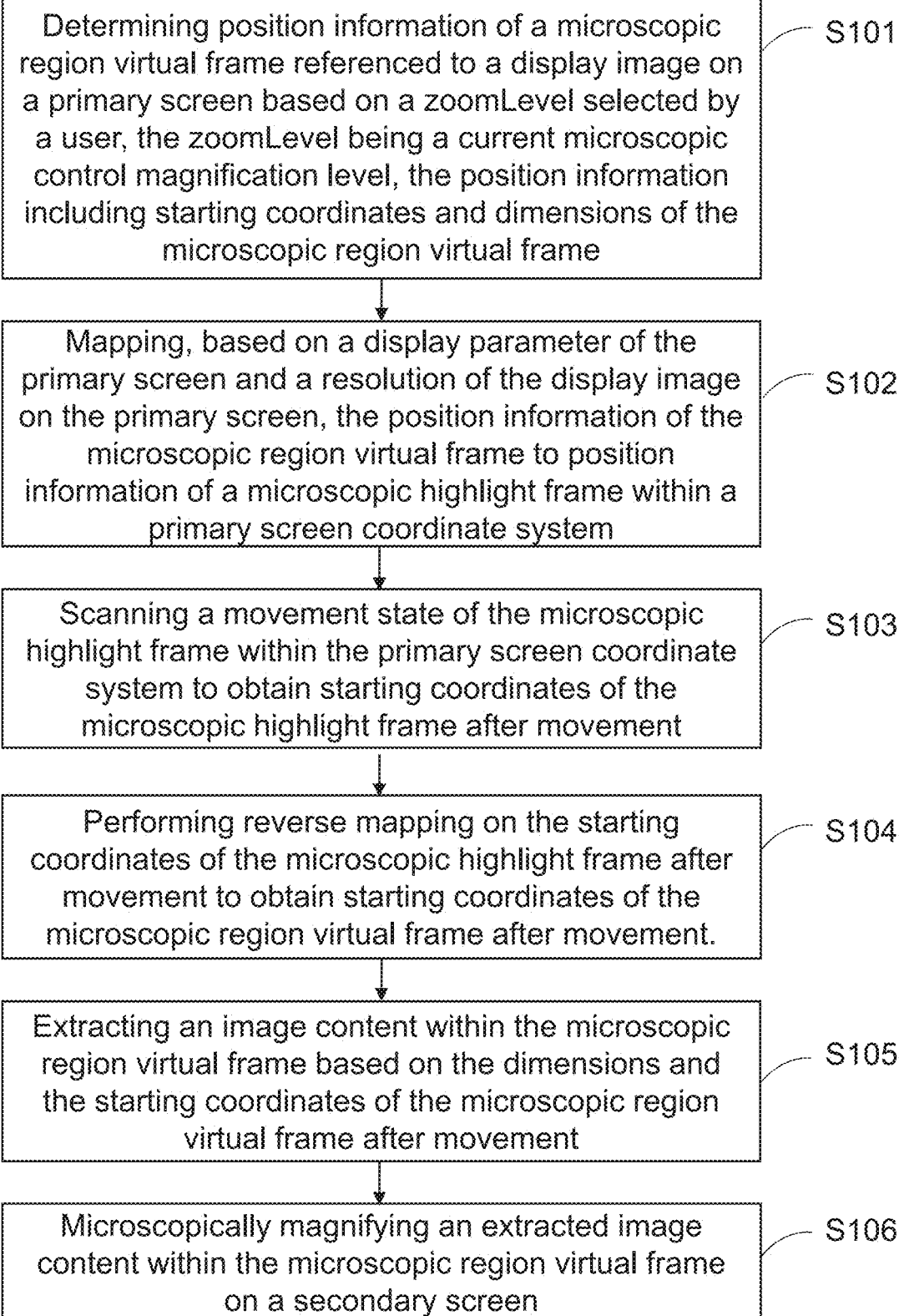

Determining position information of a microscopic region virtual frame referenced to a display image on a primary screen based on a zoomLevel selected by a user, the zoomLevel being a current microscopic control magnification level, the position information including starting coordinates and dimensions of the microscopic region virtual frame — S101

Mapping, based on a display parameter of the primary screen and a resolution of the display image on the primary screen, the position information of the microscopic region virtual frame to position information of a microscopic highlight frame within a primary screen coordinate system — S102

Scanning a movement state of the microscopic highlight frame within the primary screen coordinate system to obtain starting coordinates of the microscopic highlight frame after movement — S103

Performing reverse mapping on the starting coordinates of the microscopic highlight frame after movement to obtain starting coordinates of the microscopic region virtual frame after movement. — S104

Extracting an image content within the microscopic region virtual frame based on the dimensions and the starting coordinates of the microscopic region virtual frame after movement — S105

Microscopically magnifying an extracted image content within the microscopic region virtual frame on a secondary screen — S106

FIG. 2

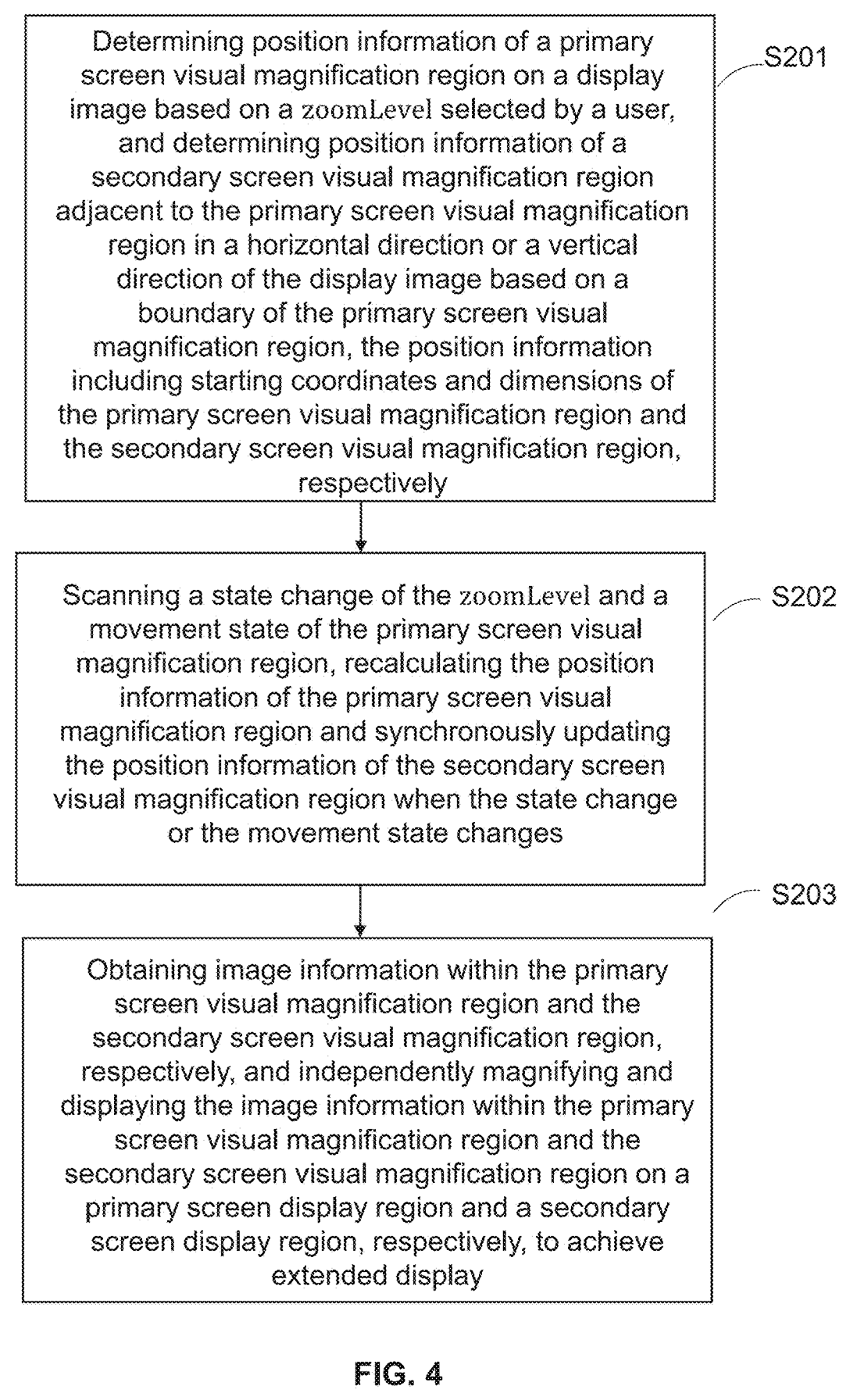

Determining position information of a primary screen visual magnification region on a display image based on a zoomLevel selected by a user, and determining position information of a secondary screen visual magnification region adjacent to the primary screen visual magnification region in a horizontal direction or a vertical direction of the display image based on a boundary of the primary screen visual magnification region, the position information including starting coordinates and dimensions of the primary screen visual magnification region and the secondary screen visual magnification region, respectively

S201

Scanning a state change of the zoomLevel and a movement state of the primary screen visual magnification region, recalculating the position information of the primary screen visual magnification region and synchronously updating the position information of the secondary screen visual magnification region when the state change or the movement state changes

S202

S203

Obtaining image information within the primary screen visual magnification region and the secondary screen visual magnification region, respectively, and independently magnifying and displaying the image information within the primary screen visual magnification region and the secondary screen visual magnification region on a primary screen display region and a secondary screen display region, respectively, to achieve extended display

FIG. 4

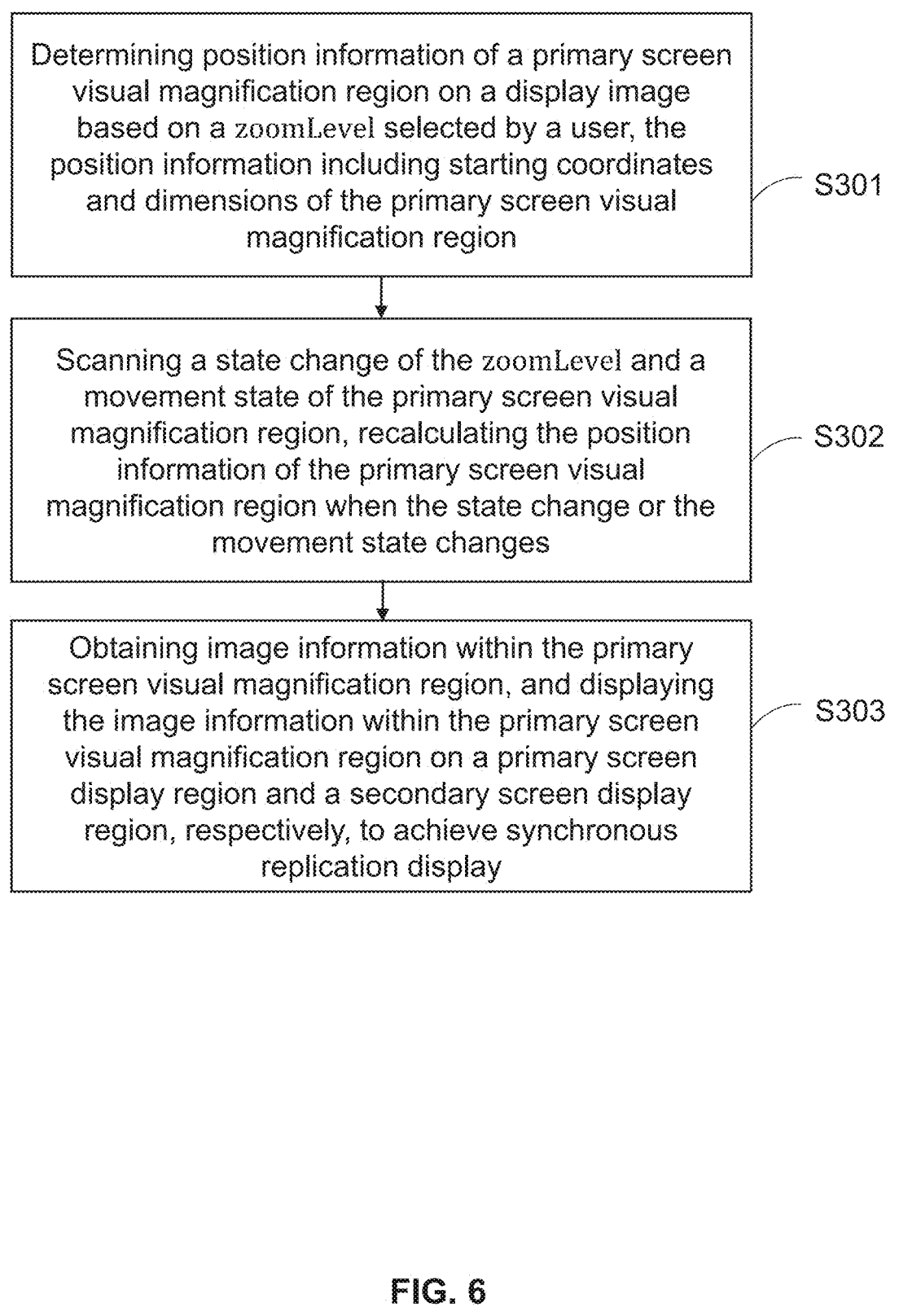

Determining position information of a primary screen visual magnification region on a display image based on a zoomLevel selected by a user, the position information including starting coordinates and dimensions of the primary screen visual magnification region ⌐ S301

Scanning a state change of the zoomLevel and a movement state of the primary screen visual magnification region, recalculating the position information of the primary screen visual magnification region when the state change or the movement state changes ⌐ S302

Obtaining image information within the primary screen visual magnification region, and displaying the image information within the primary screen visual magnification region on a primary screen display region and a secondary screen display region, respectively, to achieve synchronous replication display ⌐ S303

FIG. 6

10 — Position information determination unit

60 — Display control unit

20 — Position information mapping unit

50 — Content extraction unit

30 — State scanning and updating unit

40 — Position information reverse mapping unit

DUAL-SCREEN ASSISTIVE DISPLAY METHODS AND DEVICES SUITABLE FOR PEOPLE WITH LOW VISION AND APPARATUSES

CROSS-REFERENCE TO RELATED APPLICATIONS

This application claims priority to Chinese Patent Application No. 202410525591.8, filed on Apr. 29, 2024, the entire contents of which are incorporated herein by reference.

TECHNICAL FIELD

The present disclosure relates to the field of assistive display technology, and in particular to a dual-screen assistive display method and device suitable for people with low vision and an apparatus.

BACKGROUND

An electronic vision aid (EVA) is an assistive display device primarily designed for visually impaired individuals, comprising key components including a camera, a processor, and a display screen. The camera acquires visual data, which is then processed by the processor and rendered on the display screen with adaptive adjustments (e.g., magnification, and color contrast enhancement), which enables low-vision users (e.g., individuals with presbyopia or ophthalmic pathologies) to perceive target content with improved clarity.

Conventional EVAs mostly adopt a single-display structure. However, with the continuous advancement of assistive technology, dual-screen vision aid structures have emerged in the market. In existing dual-screen vision aids, the two displays typically present different scenes. For instance, one screen may be configured for near-viewing while the other for distance-viewing, or both screens may synchronously replicate the same content. Nevertheless, whether configured for simultaneous near/distance viewing or synchronous duplication, the maximum field of view (FOV) of each display image remains limited to the area of a single display screen. Moreover, the image on each display can only be uniformly zoomed in or out as a whole. In other words, current dual-screen vision aids not only fail to achieve FOV expansion but also cannot simultaneously display a global preview and a locally magnified view, resulting in a narrow functional scope that falls short of practical user needs.

SUMMARY

In order to overcome the deficiencies of the prior art, the present disclosure provides a dual-screen assistive display method and device suitable for people with low vision and an apparatus.

In order to achieve the above purposes, one or more embodiments of the present disclosure provide a dual-screen assistive display method suitable for people with low vision. The dual-screen assistive display method may comprise: determining position information of a microscopic region virtual frame referenced to a display image on a primary screen based on a zoomLevel selected by a user, wherein the zoomLevel is a current microscopic control magnification level, the position information includes starting coordinates $(Zoom_x, Zoom_y)$ and dimensions $(Zoom_w, Zoom_h)$ of the microscopic region virtual frame;

mapping, based on a display parameter of the primary screen and a resolution $W_0 \times H_0$ of the display image on the primary screen, the position information of the microscopic region virtual frame to position information of a microscopic highlight frame within a primary screen coordinate system, wherein the position information of the microscopic highlight frame includes starting coordinates $(OSD_x, OSD_y)$ and dimensions $(OSD_w, OSD_h)$ of the microscopic highlight frame;

scanning a movement state of the microscopic highlight frame within the primary screen coordinate system to obtain starting coordinates $(OSD_x', OSD_y')$ of the microscopic highlight frame after movement;

performing reverse mapping on the starting coordinate $(OSD_x', OSD_y')$ of the microscopic highlight frame after movement to obtain starting coordinates $(Zoom_x', Zoom_y')$ of the microscopic region virtual frame after movement;

extracting an image content within the microscopic region virtual frame based on the dimensions $(Zoom_w, Zoom_h)$ and the starting coordinates $(Zoom_x', Zoom_y')$ of the microscopic region virtual frame after movement;

microscopically magnifying an extracted image content within the microscopic region virtual frame on a secondary screen;

wherein an aspect ratio of the primary screen is 16:9 and a resolution of the primary screen is $D_w \times D_h$;

the display image is magnified using a two-stage magnification strategy based on a change in the zoomLevel selected by the user; when the zoomLevel ranges from 0 to $zoomLevel_{16R9}$, the display image is magnified using a first magnification strategy to adapt to a size of the primary screen, wherein the $zoomLevel_{16R9}$ is a magnification level at which the display image first adapts to the size of the primary screen; when the zoomLevel ranges from $zoomLevel_{16R9}$ to $zoomLevel_{max}$, the display image adapted to the size of the primary screen is proportionally magnified using a second magnification strategy, wherein the $zoomLevel_{max}$ is a maximum magnification level;

the first magnification strategy includes:

when a condition $W_o \times D_h > H_o \times D_w$ is satisfied, the position information of the microscopic region virtual frame is expressed as:

$$Zoom_w = W_o - 2 \times 32 \times ZoomLevel;$$

$$Zoom_h = H_o;$$

$$Zoom_x = Zoom_{x0} - 32;$$

$$Zoom_y = Zoom_{y0};$$

when a condition $W_o \times D_h < H_o \times D_w$ is satisfied, the position information of the microscopic region virtual frame is expressed as:

$$Zoom_w = W_o;$$

$$Zoom_h = H_o - 2 \times 32 \times ZoomLevel;$$

$$Zoom_x = Zoom_{x0};$$

$$Zoom_y = Zoom_{y0} - 32;$$

the second magnification strategy includes:

the position information of the microscopic region virtual frame is calculated upon a step of zoomLevel+1 for each microscopic control magnification level as follows:

$$Zoom_w = Zoom_{w0} - 32 \times 2;$$

$$Zoom_h = Zoom_{h0} - 32 \times 2;$$

$$Zoom_x = Zoom_{x0} - 32;$$

$$Zoom_y = Zoom_{y0} - 32;$$

where $(Zoom_{x0}, Zoom_{y0})$ and $(Zoom_{w0}, Zoom_{h0})$ are the starting coordinates and the dimensions of the microscopic region virtual frame before the change in the ZoomLevel, $(Zoom_x, Zoom_y)$ and $(Zoom_w, Zoom_h)$ are the starting coordinates and the dimensions of the microscopic region virtual frame determined based on the zoomLevel; wherein W is a width of the display image, and H is a height of the display image.

One or more embodiments of the present disclosure provide a dual-screen assistive vision display device suitable for people with low vision. The dual-screen assistive display device may comprise: a position information determination unit, a position information mapping unit, a state scanning and updating unit, a position information reverse mapping unit, a content extraction unit, and a display control unit. The position information determination unit may be configured to determine position information of a microscopic region virtual frame referenced to a display image on a primary screen based on a zoom Level selected by a user, wherein the zoom Level is a current microscopic control magnification level, the position information includes starting coordinates $(Zoom_x, Zoom_y)$ and dimensions $(Zoom_w, Zoom_h)$ of the microscopic region virtual frame. The position information mapping unit may be configured to map, based on a display parameter of the primary screen and a resolution $W_0 \times H_0$ of the display image on the primary screen, the position information of the microscopic region virtual frame to position information of a microscopic highlight frame within a primary screen coordinate system, wherein the position information of the microscopic highlight frame includes starting coordinates $(OSD_x, OSD_y)$ and dimensions $(OSD_w, OSD_h)$. The state scanning and updating unit may be configured to scan a movement state of the microscopic highlight frame within the primary screen coordinate system to obtain starting coordinates $(OSD_x', OSD_y')$ of the microscopic highlight frame after movement. The position information reverse mapping unit may be configured to perform reverse mapping on the starting coordinate $(OSD_x', OSD_y')$ of the microscopic highlight frame after movement to obtain starting coordinates $(Zoom_x', Zoom_y')$ of the microscopic region virtual frame after movement. The content extraction unit may be configured to configured to extract an image content within the microscopic region virtual frame based on the dimensions $(Zoom_w, Zoom_h)$ and the starting coordinates $(Zoom_x', Zoom_y')$ of the microscopic region virtual frame after movement. The display control unit may be configured to microscopically magnify an extracted image content within the microscopic region virtual frame on a secondary screen.

The present disclosure further provides a computer apparatus, comprising a memory and a processor. The memory may be configured to store one or more computer programs that, when executed by the processor, direct the processor to implement the dual-screen assisted vision display method suitable for people with low vision.

In some embodiments, the dual-screen assistive display method for people with low vision provided by the present disclosure further supports a dual-screen extended display mode and a dual-screen synchronous replication mode. In the dual-screen extended display mode, the secondary screen displays an image corresponding to an adjacent FOV that is continuously connected-either vertically or horizontally-to the image displayed on the primary screen, which expands the viewable content range under high magnification, effectively doubling the FOV in either the vertical or horizontal direction compared to the synchronous replication mode, thereby enhancing reading continuity.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering indicates the same structure, wherein:

FIG. 2 is a flowchart illustrating a microscopic magnification mode in FIG. 1 according to some embodiments of the present disclosure.

FIG. 4 is a flowchart illustrating an extended display mode in FIG. 1 according to some embodiments of the present disclosure.

FIG. 6 is a flowchart illustrating a synchronous replication mode in FIG. 1 according to some embodiments of the present disclosure.

DETAILED DESCRIPTION

Figure 1:
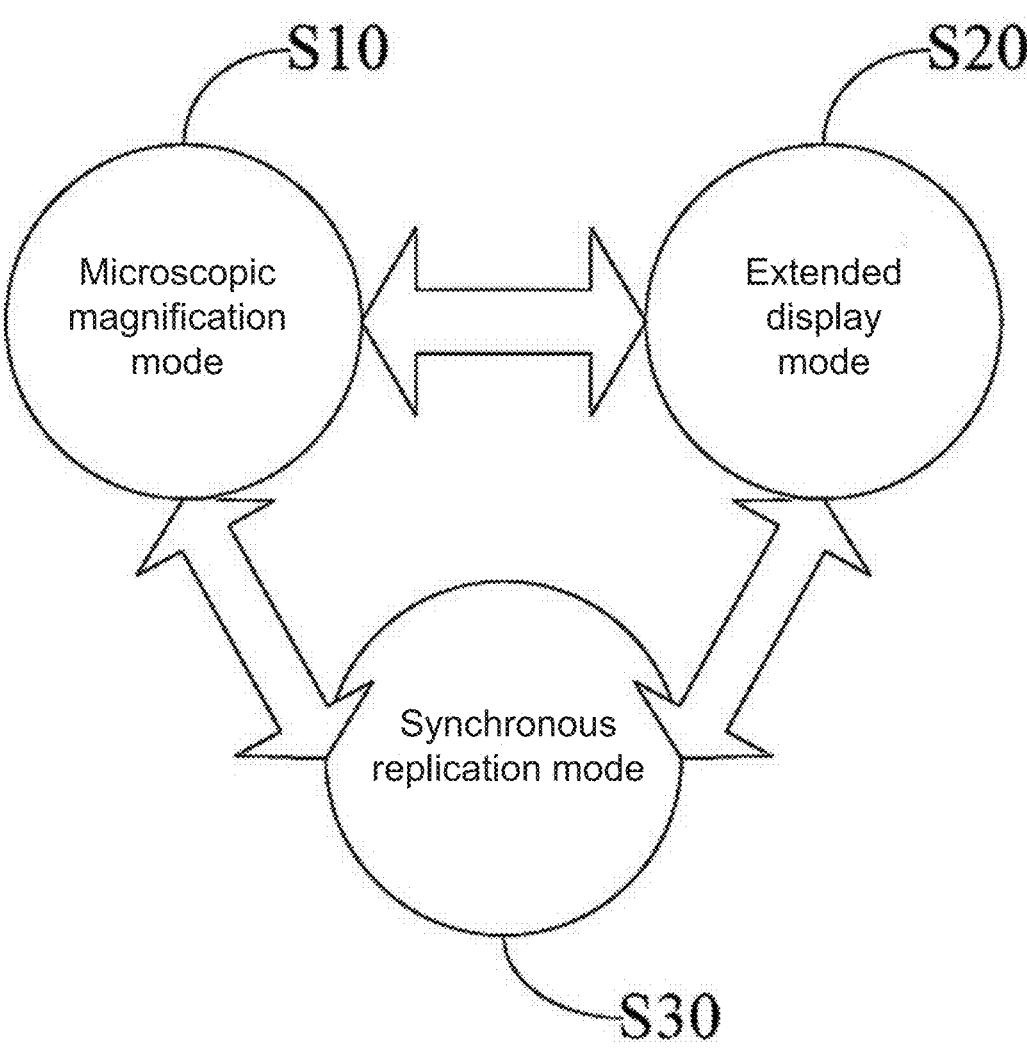
FIG. 1 is a schematic diagram illustrating multi-display mode switching of a dual-screen assistive display method suitable for people with low vision according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. Unless obviously obtained from the context or the context illustrates otherwise, the same numeral in the drawings refers to the same structure or operation.

FIG. 1 is a schematic diagram illustrating multi-display mode switching of a dual-screen assistive display method suitable for people with low vision according to some embodiments of the present disclosure. As shown in FIG. 1, the dual-screen assistive display method suitable for people with low vision provided in the present disclosure has three display modes, namely, a microscopic magnification mode S10, an extended display mode S20, and a synchronous replication mode S30. A user may switch among the three modes as needed during use, which is not limited in the present disclosure. In other embodiments, the dual-screen assistive display method for people with low vision may also have only the microscopic magnification mode S10, or combine either of the extended display mode S20 and synchronous replication mode S30 based on the microscopic magnification mode S10; or extend existing dual-screen display functions such as synchronous distance-viewing and near-viewing (implemented by using dual cameras) based on the microscopic magnification mode S10.

As shown in FIG. 1, the dual-screen assistive display method for people with low vision provided in the present disclosure includes the following operations in the microscopic magnification mode S10:

S101, determining position information of a microscopic region virtual frame referenced to a display image on a primary screen based on a zoomLevel selected by a user, wherein the zoomLevel is a current microscopic control magnification level, the position information includes starting coordinates ($Zoom_x$, $Zoom_y$) and dimensions ($Zoom_w$, $Zoom_h$) of the microscopic region virtual frame.

The display image is an original image that needs to be magnified for display. The zoomLevel refers to magnification of the display image. For example, zoomLevel=2 means that the display image is magnified by 2 times.

In some embodiments, a processor may determine a dimensional relationship between the microscopic region virtual frame and the display image based on the zoomLevel, and determine dimensions ($Zoom_w$, $Zoom_h$) of the microscopic region virtual frame based on the dimensional relationship. The processor may construct a display image coordinate system based on a resolution $W_0 \times H_0$ of the display image, and determine starting coordinates selected from the display image by the user as the starting coordinates ($Zoom_x$, $Zoom_y$) of the microscopic region virtual frame.

S102, mapping, based on a display parameter of the primary screen and a resolution $W_0 \times H_0$ of the display image on the primary screen, the position information of the microscopic region virtual frame to position information of a microscopic highlight frame within a primary screen coordinate system, wherein the position information of the microscopic highlight frame includes starting coordinates ($OSD_x$, $OSD_y$) and dimensions ($OSD_w$, $OSD_h$) of the microscopic highlight frame within the primary screen coordinate system.

The primary screen coordinate system is a 2D coordinate system established based on the resolution of the primary screen. In some embodiments, an upper left corner of the primary screen may be taken as an origin of the primary screen coordinate system, where a direction rightward from the origin is an x-axis positive direction, and a direction downward from the origin is a y-axis positive direction.

The mapping is an operation of mapping the display image coordinate system to the primary screen coordinate system.

S103, scanning a movement state of the microscopic highlight frame within the primary screen coordinate system to obtain starting coordinates ($OSD_x'$, $OSD_y'$) of the microscopic highlight frame after movement.

S104, performing reverse mapping on the starting coordinates ($OSD_x'$, $OSD_y'$) of the microscopic highlight frame after movement to obtain starting coordinates ($Zoom_x'$, $Zoom_y'$) of the microscopic region virtual frame after movement.

The reverse mapping is an operation of mapping the position information of the primary screen coordinate system to the display image coordinate system.

S105, extracting an image content within the microscopic region virtual frame based on the dimensions ($Zoom_w$, $Zoom_h$) and the starting coordinates ($Zoom_x'$, $Zoom_y'$) of the microscopic region virtual frame after movement.

The image content is a content that needs to be displayed in the microscopic region virtual frame. In some embodiments, the processor may determine a position of the microscopic region virtual frame within the display image based on the dimensions ($Zoom_w$, $Zoom_h$) of the microscopic region virtual frame and the starting coordinates ($Zoom_x'$, $Zoom_y'$) of the microscopic region virtual frame after movement, and intercept the display image within the position as the image content within the microscopic region virtual frame.

S106, microscopically magnifying an extracted image content within the microscopic region virtual frame on a secondary screen.

In some embodiments, the starting coordinates of the microscopic region virtual frame are coordinates of an upper left corner of the microscopic region virtual frame. ($Zoom_x+Zoom_w$, $Zoom_y+Zoom_h$) are endpoint coordinates of the microscopic region virtual frame. Correspondingly, the starting coordinates ($OSD_x$, $OSD_y$) of the microscopic highlight frame are coordinates of an upper left corner of the microscopic highlight frame, and ($OSD_x+OSD_w$, $OSD_y+OSD_h$) are endpoint coordinates of the microscopic highlight frame, which is not limited in the present disclosure. In some embodiments, coordinates of a lower left corner of the microscopic region virtual frame may be defined as the starting coordinates.

In some embodiments, an aspect ratio of the primary screen is 16:9 and a resolution of the primary screen is $D_w \times D_h$; the display image is magnified using a two-stage magnification strategy based on a change in the zoomLevel selected by the user. When the zoomLevel ranges from 0 to $zoomLevel_{16R9}$, the display image is magnified using a first magnification strategy to adapt to a size of the primary screen, where the $zoomLevel_{16R9}$ is a magnification level at which the display image first adapts to the size of the primary screen. When the zoomLevel ranges from $zoomLevel_{16R9}$ to $zoomLevel_{max}$, the display image adapted to the size of the primary screen is proportionally magnified using a second magnification strategy.

The present disclosure is illustrated with the aspect ratio of the primary screen being 16:9. However, the size of the primary screen is not limited in the present disclosure. In other embodiments, other sizes of the primary screens may be used; the display image may be magnified using the two-stage magnification strategy, a three-stage magnification strategy, or the like. The two-stage magnification strategy provided in this embodiment is described in detail below. $zoomLevel_{16R9}$ and $zoomLevel_{max}$ may be determined based on prior experience.

When the microscopic magnification mode is implemented, the $\text{ZoomLevel}_{16R9}$ at which the display image first adapts to the size (e.g., 16:9) of the primary screen in the microscopic magnification mode, and the $\text{ZoomLevel}_{max}$ supported by the microscopic magnification mode are determined first.

In some embodiments, when a condition $(W_o \times D_h \geq H_o \times D_w)$ is satisfied:

$$zoomLevel_{16R9} = (W_0 - H_0 \times D_w \div D_h) \div 32 \div 2;$$

$$zoomLevel_{max} = zoomLevel_{16R9} + (H_0 - 192) \div 18 \div 2.$$

In some embodiments, when the condition $(W_o \times D_h \geq H_o \times D_w)$ is not satisfied:

$$zoomLevel_{16R9} = (H_0 - W_0 \times D_h \div D_w) \div 32 \div 2;$$

$$zoomLevel_{max} = zoomLevel_{16R9} + (W_0 - 192) \div 36 \div 2.$$

Whether the condition is satisfied is determined and then the size of the ZoomLevel is determined. When the ZoomLevel from 0 to $zoomLevel_{16R9}$, the first magnification strategy includes:

when the condition $(W_o \times D_h \geq H_o \times D_w)$ is satisfied, using a horizontal stepping strategy, the position information of the microscopic region virtual frame being adjusted according to the following equation:

$$Zoom_w = W_o - 2 \times 32 \times ZoomLevel;$$

$$Zoom_h = H_o;$$

$$Zoom_x = Zoom_{x0} - 32;$$

$$Zoom_y = Zoom_{y0};$$

when a condition $(W_o \times D_h < H_o \times D_w)$ is satisfied, the position information of the microscopic region virtual frame is adjusted according to the following equation:

$$Zoom_w = W_o;$$

$$Zoom_h = H_o - 2 \times 32 \times ZoomLevel;$$

$$Zoom_x = Zoom_{x0};$$

$$Zoom_y = Zoom_{y0} - 32.$$

In some embodiments, when the zoomLevel ranges from $zoomLevel_{16R9}$ to $zoomLevel_{max}$, a second magnification strategy is adopted; the position information of the microscopic region virtual frame is calculated upon a step of zoomLevel+1 for each microscopic control magnification level as follows:

$$Zoom_w = Zoom_{w0} - 32 \times 2;$$

$$Zoom_h = Zoom_{h0} - 32 \times 2;$$

-continued
$$Zoom_x = Zoom_{x0} - 32;$$

$$Zoom_y = Zoom_{y0} - 32;$$

where $(Zoom_{x0}, Zoom_{y0})$ and $(Zoom_{w0}, Zoom_{h0})$ are starting coordinates and dimensions of the microscopic region virtual frame of a previous zoomLevel, $(Zoom_x, Zoom_y)$ are the starting coordinates of the microscopic region virtual frame determined based on the zoom-Level. When entering the microscopic magnification mode for the first time, $Zoom_{x0}=Zoom_{x0}'$; $Zoom_{y0}=Zoom_{y0}'$; $Zoom_{w0}=Zoom_{w0}'$; $Zoom_{h0}=Zoom_{h0}'$.

According to the dual-screen assistive display method suitable for people with low vision provided in some embodiments of the present disclosure, the position information of the microscopic region virtual frame referenced to the display image on the primary screen is determined based on the zoomLevel selected by the user, the image content of the display image within the microscopic region virtual frame is extracted and microscopically magnified on the secondary screen, thereby realizing the global preview on the primary screen and the locally magnified view on the secondary screen.

When the microscopic region virtual frame is moved to change the microscopic magnified content, the present disclosure converts the position information of the microscopic region virtual frame which is affected by the image parameter and difficult to be scanned and localized into the position information of the microscopic highlight frame within the standard primary screen coordinate system based on the mapping relationship between the position information of the microscopic region virtual frame and the position information of the microscopic highlight frame. The method locates the microscopic highlight region on the primary screen display region instead of locating the microscopic magnified content on the display image. After the position information of the microscopic highlight region after movement is determined, the position information of the microscopic region virtual frame is obtained by performing the reverse mapping.

Finally, the microscopic magnified content is extracted from the microscopic region virtual frame after the mapping and displayed on the secondary screen. This microscopic magnification mode realizes the global preview and local magnification, and greatly reduces the difficulty of microscopic magnification positioning, thereby greatly improving the response speed of the microscopic magnification of the secondary screen.

Figure 3:
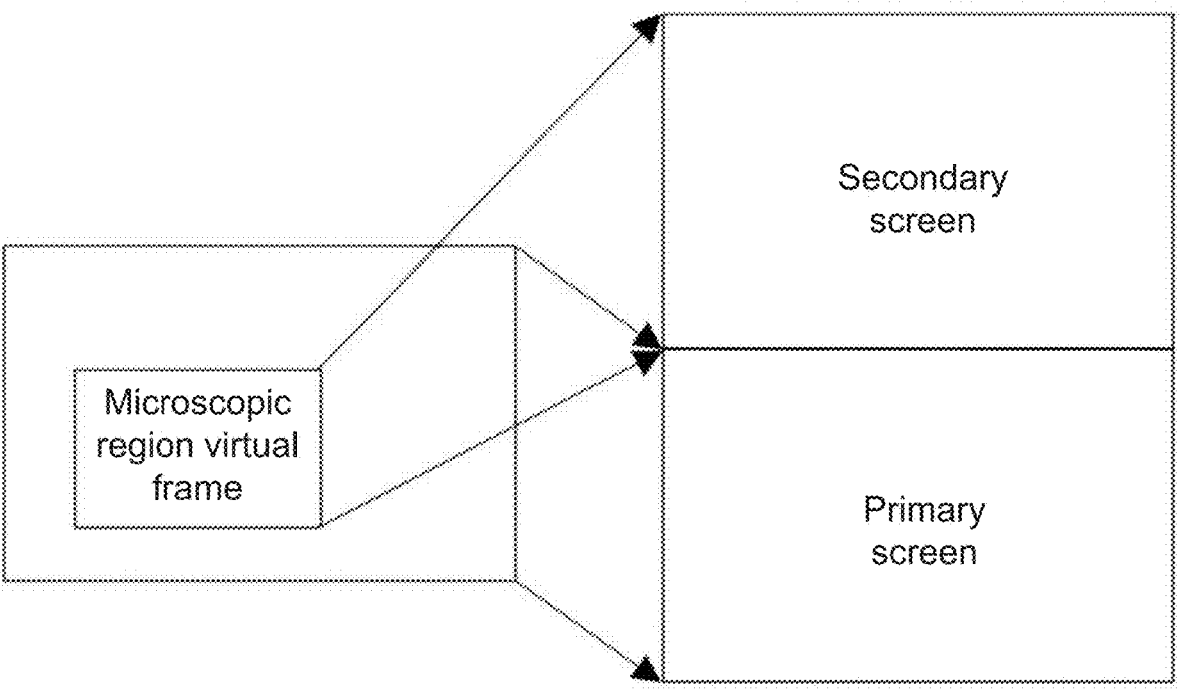
FIG. 3 is a schematic diagram illustrating a principle of the microscopic magnification mode in FIG. 1 according to some embodiments of the present disclosure.

The dual-screen assistive display method suitable for people with low vision provided in the present disclosure will be described in detail below with reference to FIGS. 1-3.

FIG. 2 is a flowchart illustrating a microscopic magnification mode in FIG. 1 according to some embodiments of the present disclosure. FIG. 3 is a schematic diagram illustrating a principle of the microscopic magnification mode in FIG. 1 according to some embodiments of the present disclosure.

As shown in FIG. 2, the microscopic magnification mode S10 includes S101: determining a position of a microscopic region virtual frame on a display image based on a zoom Level selected by a user.

In some embodiments, the S101 includes: S1011, determining a visual coordinate region of an image with a resolution of $D_w \times D_h$ on a primary screen, where a resolution of the image is denoted as $W_0 \times H_0$, in the microscopic magnification mode, it needs to ensure that all image information and outlines are displayed on the primary screen to achieve a global preview. This embodiment defines starting coordinates of a global visual region window on the primary screen as $(X_o, Y_o)$ and dimensions of the global visual region window as $(DW_o, DH_o)$.

In some embodiments, when a condition $(W_o \times D_h \geq H_o \times D_w)$ is satisfied, the starting coordinates and the dimensions of the global visual region window are calibrated as follows:

$$DW_0 = D_w;$$

$$DH_0 = (H_0 \times D_w \div W_o) \, \&0xFFFE;$$

$$X_0 = ((D_w - DW_0) \gg 1) \, \&0xFFFE;$$

$$Y_0 = ((D_H - DH_0) \gg 1) \, \&0xFFFE.$$

In some embodiments, when a condition $(W_o \times D_h < H_o \times D_w)$ is satisfied, the starting coordinates and the dimensions of the global visual region window are calibrated as follows:

$$DW_0 = (W_0 \times D_h \div H_o) \, \&0 \times FFFE;$$

$$DH_0 = D_h;$$

$$X_0 = ((D_w - DW_0) \gg 1) \, \&0 \times FFFE;$$

$$Y_0 = ((D_H - DH_0) \gg 1) \, \&0 \times FFFE.$$

where &0xFFFE means conversion to binary.

S1012, after the starting coordinates and the dimensions of the global visual region window on the primary screen are determined, determining initial coordinates and initial dimensions of the microscopic region virtual frame upon initial entry into the microscopic magnification mode. In some embodiments, $zoomLevel_0$ is defined as a current microscopic control magnification level, $zoomLevel_0 = zoomLevel_{max}/2$ when entering the microscopic magnification mode, where $zoomLevel_{max}$ is a maximum zoomLevel supported by the microscopic magnification mode, which is not limited in the present disclosure. In other embodiments, $ZoomLevel_0$ may be selected as other proportion parameters of $zoomLevel_{max}$, such as $\frac{1}{3}$, $\frac{1}{4}$, or $\frac{1}{5}$, etc.

According to the determined initial $ZoomLevel_0$, if $(W_o \times D_h \geq H_o \times D_w)$, the dimensions $(Zoom_{wo}', Zoom_{ho}')$ of the microscopic region virtual frame upon initial entry into the microscopic magnification mode is determined using the following equation:

$$Zoom'_{w0} = W_o - 2 \times 32 \times zoomLevel_0;$$

$$Zoom'_{h0} = H_o;$$

if $(W_o \times D_h < H_o \times D_w)$, the dimensions $(Zoom_{wo}', Zoom_{ho}')$ of the microscopic region virtual frame upon initial entry into the microscopic magnification mode is determined using the following equation:

$$Zoom'_{w0} = W_o;$$

-continued
$$Zoom'_{h0} = H_o - 2 \times 32 \times zoomLevel_0.$$

Mapping coordinates $(x_o, y_o)$ of the starting coordinates $(X_o, Y_o)$ of the global visual region window on the primary screen within a virtual coordinate system referenced to the image are used as the initial coordinates of the microscopic region virtual frame upon initial entry into the microscopic magnification mode; the coordinates $(X_o, Y_o)$ and the coordinates $(x_o, y_o)$ may be obtained by mapping based on an inverse mapping relationship of S103. That is, the coordinates $(Zoom_{xo}', Zoom_{yo}')$ of the microscopic region virtual frame in an initial state are the coordinates $(x_o, y_o)$, which is not limited in the present disclosure. In other embodiments, mapping coordinates of a center of the global visual region window on the primary screen within the virtual coordinate system referenced to the image may be used as the initial coordinates of the microscopic region virtual frame upon initial entry into the microscopic magnification mode.

S1013, determining a magnification strategy of the microscopic region virtual frame in the microscopic magnification mode to obtain the position information of the microscopic region virtual frame after adjustment of the zoomLevel.

In some embodiments, an adjustment range of the zoomLevel is in a range of $0$-$ZoomLevel_{max}$, and the $ZoomLevel_{max}$ is correlated with the resolution of the display image and the resolution of the primary screen.

In some embodiments, the $ZoomLevel_{max}$ is positively correlated to the resolution of the display image and the resolution of the primary screen. For example, a larger resolution of the display image indicates that the display image still maintains good clarity after high magnification, in this case, a relatively large $ZoomLevel_{max}$ may be set; the larger the resolution of the primary screen, the more information is displayed on the primary screen, in this case, a relatively large $zoomLevel_{max}$ may be set to fully magnify the display image.

In the present disclosure, in order to adapt different sizes of display images to the global visual region window within the primary screen, the display image is magnified based on the zoomLevel selected by the user using a two-stage magnification strategy.

In some embodiments, when the zoomLevel ranges from $zoomLevel_{16R9}$ to $zoomLevel_{max}$, the display image adapted to the size of the primary screen is proportionally magnified using a first magnification strategy, then the processor determines a first image feature based on the image content of the display image; and determines a virtual frame adjustment quantity based on the first image feature.

The first image feature reflects an attribute feature of the image content. In some embodiments, the first image feature may include at least one of a text dense feature (e.g., a text density, a paragraph spacing, and line spacing), an image texture feature (e.g., a line texture in an image), an image color distribution (e.g., a color histogram), or the like.

In some embodiments, the processor may obtain the first image feature by recognizing the image content through an image recognition model. The image recognition model may be a machine learning model. In some embodiments, the image recognition model may be an existing model, such as YOLOv8, Detectron2, etc. In some embodiments, the image recognition model may be configured to recognize an image edge of the image content, a second image feature, etc.

The virtual frame adjustment quantity is a parameter used to adjust a size of the virtual frame. In some embodiments, the virtual frame adjustment quantity may include a vertical adjustment quantity and a horizontal adjustment quantity. The vertical adjustment quantity may include an adjustment direction and an adjustment magnitude for an upper boundary and a lower boundary of the virtual frame; the horizontal adjustment quantity may include an adjustment direction and an adjustment magnitude for a left boundary and a right boundary of the virtual frame. Movement and zooming of the virtual frame may be realized by setting the appropriate virtual frame adjustment quantity.

In some embodiments, the processor may determine the virtual frame adjustment quantity based on the first image feature through an adjustment quantity prediction model.

The adjustment quantity prediction model is a model for determining the virtual frame adjustment quantity. In some embodiments, the adjustment quantity prediction model may be a machine learning model.

In some embodiments, an input of the adjustment quantity prediction model may include the first image feature, and an output of the adjustment quantity prediction model may include the virtual frame adjustment quantity.

In some embodiments, the adjustment quantity prediction model may be obtained by training based on a large number of first training samples with first labels.

The first training samples may include a sample first image feature. The first labels may be a sample virtual frame adjustment quantity corresponding to the first training sample In some embodiments, the processor may obtain a large amount of historical image contents from historical data and determine whether a user adjustment record exists in the historical image contents. The user adjustment record is a record where the user manually adjusts a position or a size of a historical virtual frame displaying the historical image contents.

In some embodiments, for each historical image content for which the user adjustment record exists, the processor may recognize the historical image content using the image recognition model, and use a historical first image feature of the historical image content as the sample first image feature. The processor may obtain, based on the user adjustment record, an adjustment direction and an adjustment magnitude of an upper boundary, a lower boundary, a left boundary, and a right boundary of the historical virtual frame displaying the historical image content to be used as the first labels corresponding to the first samples.

In some embodiments, the adjustment quantity prediction model may be obtained by training in the following way. The processor may input a plurality of first training samples with the first labels into an initial adjustment quantity prediction model, construct a loss function through the first labels and output results of the initial adjustment quantity prediction model, and iteratively updating parameters of the initial adjustment quantity prediction model based on the loss function. The model training is completed when the loss function of the initial adjustment quantity prediction model satisfies an iteration condition, and a trained adjustment quantity prediction model is obtained. The iteration condition may be that the loss function converges, a count of iterations reaches a threshold, etc.

In some embodiments of the present disclosure, by determining the virtual frame adjustment quantity to dynamically adjust the size and the position of the virtual frame in real time, it ensures that when the size and the position of the virtual frame do not meet the expectations of the user, the adjustment can be made quickly and automatically, helping the user to focus on core information and reduce visual burden for the user.

In some embodiments, the processor may determine the virtual frame adjustment quantity based on the first image feature and a user eyestrain value.

The user eyestrain value reflects an eyestrain level of the user. The larger the user eyestrain value, the greater the eyestrain level of the user. The processor may determine the user eyestrain value based on user eye movement data. For example, the slower the blinking frequency, the greater the eyestrain value; the longer the gaze duration, the greater the eyestrain value.

In some embodiments, the input of the adjustment quantity prediction model may further include the user eyestrain value, and the first training samples may further include a sample user eyestrain value.

In some embodiments of the present disclosure, dynamically adjusting the virtual frame based on the eyestrain level ensures that a mode determination model considers the eyestrain level of the user, which helps to alleviate ocular stress.

In some embodiments of the present disclosure, by analyzing user preferences, usage habits, and automatically switching to the display mode preferred by the user, the manual operation can be reduced.

In some embodiments, the processor may determine, based on the first image feature, weights of different content types in the second image feature; and determine, based on the weights of the different content types in the second image feature, the virtual frame adjustment quantity.

In some embodiments, the processor may obtain the weight of at least one of the contents in the second image feature based on the first image feature through a large language model. More descriptions regarding the second image feature may be found in the present disclosure below.

In some embodiments, the input of the adjustment quantity prediction model may further include the weights of the different content types in the second image feature, and the first training samples may further include sample weights of the different content types in the second image feature.

By inputting the weights of the different content types in the second image feature into the adjustment quantity prediction model, it ensures that the mode determination model can consider a distribution of the different content types, which helps to determine an appropriate target mode and improve the prediction accuracy of the adjustment quantity prediction model.

S102, mapping, based on a display parameter of the primary screen and a resolution of the display image on the primary screen, the position information of the microscopic region virtual frame to position information of a microscopic highlight frame within a primary screen coordinate system.

In some embodiments, the S102 is performed after the position information of the microscopic region virtual frame is determined based on the zoomLevel in the S101: determining position information of a microscopic highlight frame mapped corresponding to the microscopic region virtual frame at each magnification level on the primary screen with a resolution of $D_w \times D_h$, the position information of the microscopic highlight frame including the starting coordinates ($OSD_x$, $OSD_y$) and the dimensions ($OSD_w$, $OSD_h$) of the microscopic highlight frame.

In some embodiments, the display parameter of the primary screen includes: the starting coordinates ($X_o$, $Y_o$) and the dimensions ($DW_o$, $DH_o$) of the global visual region window when all the image information and outlines are displayed on the primary screen, where the position information of the microscopic region virtual frame is mapped to the position information of the microscopic highlight frame according to the display parameter of the primary screen and the resolution $W_0 \times H_0$ of the display image on the primary screen based on the following mapping relationship:

$$OSD_w = Zoom_w \times DW_o / W_o;$$

$$OSD_h = Zoom_h \times DH_o / H_o;$$

$$OSD_x = X_o + Zoom_x \times DW_o / W_o;$$

$$OSD_y = Y_o + Zoom_y \times DH_o / H_{o\infty}$$

S103, scanning a movement state of the microscopic highlight frame within the primary screen coordinate system to obtain starting coordinates of the microscopic highlight frame after movement.

In some embodiments, the S103 is performed after the position information of the microscopic highlight frame within the primary screen coordinate system is determined in the S102: scanning a movement state of the microscopic highlight frame within the primary screen coordinate system to obtain starting coordinates $(OSD_x', OSD_y')$ of the microscopic highlight frame after movement.

In some embodiments of the present disclosure, the position information of the microscopic region virtual frame referenced to the display image is mapped to the position information of the microscopic highlight frame referenced to the primary screen coordinate system, by scanning the position state of the microscopic highlight frame, the scanning of the change in the position state of the microscopic region virtual frame can be realized. The primary screen coordinate system is a standard rectangular coordinate system related only to the display parameter of the primary screen, and is not related to the state (e.g., an angle, clarify, and other parameters of the image) of the display image, which greatly reduces the difficulty of microscopic positioning, greatly improves the speed and accuracy of positioning, and greatly improves the response speed of microscopic magnification of the secondary screen. The positioning of the starting coordinates of the microscopic highlight frame within the primary screen may adopt an existing cursor positioning function, such as SetConsoleCursorPosition in the windows system.

In some embodiments, when scanning the movement state of the microscopic highlight frame within the primary screen coordinate system, whether the starting coordinates and the endpoint coordinates of the microscopic highlight frame exceed the global visual region window when all the image information and outlines are displayed on the primary screen may be determined; if the starting coordinates and the endpoint coordinates of the microscopic highlight frame exceed the global visual region window when all the image information and outlines are displayed on the primary screen, the starting coordinates or the endpoint coordinates may be clamped to boundary coordinates of the global visual region window to form the position information of the microscopic highlight frame after movement.

In some embodiments, if the determination indicates that the starting coordinates $(OSD_x', OSD_y')$ of the microscopic highlight frame exceed a left boundary coordinate $X_o$ of the global visual region window, the left boundary coordinate $X_o$ of the global visual region window is used as a horizontal coordinate of the microscopic highlight frame for correction, and corrected starting coordinates of the microscopic highlight frame are denoted as $(X_o, OSD_y')$. Similarly, if the determination indicates that the endpoint coordinates $(OSD_x'+OSD_w, OSD_y'+OSD_h)$ of the microscopic highlight frame exceed a right boundary coordinate $X_o+DW_o$ and an upper boundary of the global visual region window, corrected starting coordinates of the microscopic highlight frame are denoted as $(X_o+DW_o, Y_o)$. If the determination indicates that the endpoint coordinates $(OSD_x'+OSD_w, OSD_y'+OSD_h)$ of the microscopic highlight frame exceed a right boundary coordinate $X_o+DW_o$ and a lower boundary coordinate $Y_o+DH_o$ of the global visual region window, the corrected starting coordinates of the microscopic highlight frame are denoted as $(X_o+DW_o, Y_o+DH_o)$. The boundary of the microscopic highlight frame is corrected based on the boundary coordinates of the global visual region window, so that the secondary screen can accurately display the image content within the microscopic region virtual frame.

S104, performing reverse mapping on the starting coordinate of the microscopic highlight frame after movement to obtain starting coordinates of the microscopic region virtual frame after movement.

In some embodiments, the S104 is performed after the starting coordinates $(OSD_x', OSD_y')$ of the microscopic highlight frame after movement are obtained in the S103, and the reverse mapping is performed on the starting coordinates $(OSD_x', OSD_y')$ of the microscopic highlight frame after movement to obtain the starting coordinates $(Zoom_x', Zoom_y')$ of the microscopic region virtual frame.

In some embodiments, the mapping is performed using the following reverse mapping relationship:

$$Zoom_x' = ((OSD_x' - X_o) \times W_o \div DW_o) \& 0 \times FFFC;$$

$$Zoom_y' = ((OSD_y' - Y_o) \times W_o \div DW_o) \& 0 \times FFFC.$$

S105, extracting an image content within the microscopic region virtual frame based on the dimensions and the starting coordinates of the microscopic region virtual frame after movement.

In some embodiments, on this basis, the position information of the microscopic region virtual frame after movement is obtained in combination with the dimensions $(Zoom_w, Zoom_h)$ of the microscopic region virtual frame calculated based on the zoomLevel in the S101, and the image content within the microscopic region virtual frame is extracted (S105).

S106, microscopically magnifying an extracted image content within the microscopic region virtual frame on a secondary screen.

In some embodiments, after the image content within the microscopic region virtual frame is obtained in the S105, the image content is sent to the secondary screen and microscopically magnified on the secondary screen.

In some embodiments, the microscopically magnifying on the secondary screen requires to determine starting coordinates $(DISP_x, DISP_y)$ and dimensions $(DISP_w, DISP_h)$ of a microscopic magnification region on the secondary screen with a resolution of $D_w' \times D_h'$.

When the condition $(W_o \times D_h \geq H_o \times D_w)$ is satisfied, a coordinate calculation equation is expressed as:

$$DISP_w = D'_w;$$

$$DISP_h = (Zoom_w \times D'_w \div Zoom_h)\ \&0 \times FFFE;$$

$$DISP_x = ((D_w - DW_0) \gg 1)\ \&0 \times FFFE;$$

$$DISP_y = ((D_H - DH_0) \gg 1)\ \&0 \times FFFE.$$

When the condition ($W_o \times D_h \geq H_o \times D_w$) is not satisfied, the coordinate calculation equation is expressed as:

$$DISP_w = (Zoom_w \times D'_w \div Zoom_h)\ \&0 \times FFFE;$$

$$DISP_h = D'_h;$$

$$DISP_x = ((D'_w - DISP_w) \gg 1)\ \&0 \times FFFE;$$

$$DISP_y = ((D'_w - DISP_h) \gg 1)\ \&0 \times FFFE.$$

In some embodiments, the processor may determine an edge enhancement intensity based on a user vision feature, and perform edge enhancement on the image content within the virtual frame based on the edge enhancement intensity.

The user vision feature reflects the quality of user vision. The user vision feature may include an FOV, vision clarity, a contrast sensitivity, or the like, of the user. In some embodiments, the user vision feature may be determined based on user pre-input.

The edge enhancement intensity is a parameter used to enhance an edge of the display image content. The greater the edge enhancement intensity, the greater the contrast between the image content within the virtual frame and an original image content, and the more conspicuous the outline edge of the image content within the virtual frame.

In some embodiments, the processor may determine the edge enhancement intensity based on the user vision feature. For example, the worse the user vision feature (e.g., the narrower the FOV, the lower the visual clarity, the more severe the symptoms of myopia and color weakness, etc.), the greater the edge enhancement intensity. When the user vision feature is poor, the perception of the user for the image content is low, and the processor performs appropriate edge enhancement on the image content, which can better emphasize the image content within the virtual frame for the user to view.

In some embodiments, the processor may recognize the edge of the image content through an image recognition model, and perform the edge enhancement based on the edge enhancement intensity. More descriptions regarding the image recognition model may be found in present disclosure above.

In some embodiments, when the image content after the edge enhancement is fused with the original image content, the processor may dynamically adjust a weight of the fusion of the image content after the edge enhancement with the original image content based on the edge enhancement intensity. The greater the edge enhancement intensity, the greater the proportion of the image content after the edge enhancement in a final display image.

In some embodiments of the present disclosure, personalized adjustments based on the user vision feature and the edge enhancement can better highlight the text or object outlines, making the user have a better experience and better access to the information.

In some embodiments of the present disclosure, after the starting coordinates ($DISP_x, DISP_y$) and the dimensions ($DISP_w, DISP_h$) of the microscopic magnification region are determined on the secondary screen, the image content within the microscopic region virtual frame obtained by the S105 is proportionally magnified and displayed on the secondary screen, which realizes the global preview of the primary screen and the local microscopic magnification on the secondary screen, and provides two different display FOVs for the user with low vision, thereby achieving a better use experience.

In some embodiments, after the image content within the microscopic region virtual frame is extracted, color change treatment may be performed on the image content based on a background color selected by the user before microscopic magnification on the secondary screen.

In some embodiments, the processor may perform the color change treatment the image content in various ways. For example, when the image content contains a white text against a light color background, the user may select a black background, and the processor may convert the white text into a black text based on the black background. As another example, if the user is a red-green colorblind patient, the user may select an orange-blue background, and the processor may convert red and green colors in the image content into orange and blue colors, respectively; if the user is a panchromatic colorblind patient, the user may select a black-white background, and the processor may process perform black-white treatment, increase the contrast of the image content, etc.

In some embodiments of the present disclosure, by performing the color change treatment on the image content based on the background color selected by the user and then microscopically magnifying the image content on the secondary screen, it is more conducive to the reading of people with low vision who are affected by the color, thereby broadening the scope of applications of the dual-screen assistive display method.

In some embodiments, the dual-screen assistive display method suitable for people with low vision may further include the extended display mode S20.

FIG. 4 is a flowchart illustrating an extended display mode in FIG. 1 according to some embodiments of the present disclosure. As shown in FIG. 4, the extended display mode S20 includes operations S201-S203:

S201, determining position information of a primary screen visual magnification region on a display image based on a zoomLevel selected by a user, and determining position information of a secondary screen visual magnification region adjacent to the primary screen visual magnification region in a horizontal direction or a vertical direction of the display image based on a boundary of the primary screen visual magnification region, the position information including starting coordinates and dimensions of the primary screen visual magnification region and the secondary screen visual magnification region, respectively.

Figure 5:
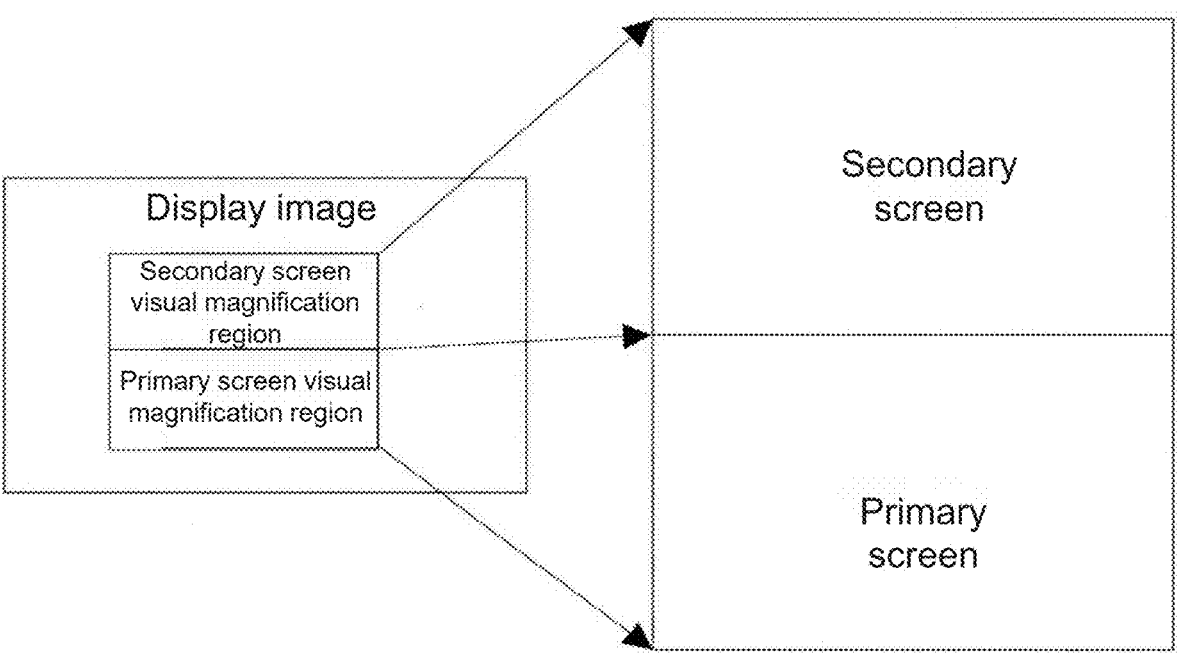
FIG. 5 is a schematic diagram illustrating a principle of the extended display mode in FIG. 4 according to some embodiments of the present disclosure.

FIG. 5 is a schematic diagram illustrating a principle of the extended display mode in FIG. 4 according to some embodiments of the present disclosure. As shown in FIG. 5, the position information of the secondary screen visual magnification region may be determined in a vertical direction of the primary screen visual magnification region by taking an upper boundary or a lower boundary of the primary screen visual magnification region as a reference; or the position information of the secondary screen visual magnification region may be determined in a horizontal direction of the primary screen visual magnification region by taking a left boundary or a right boundary of the primary screen visual magnification region as a reference.

In some embodiments of the present disclosure, a dual-screen assistive display device suitable for people with low vision may be configured to store and memorize the zoom-Level, including the zoomLevel familiar to the user or the zoomLevel at the time of last operation. According to the storage of the zoomLevel, when the user enters the extended display mode, the zoomLevel of the last mode (e.g., the microscopic magnification mode or the synchronous replication mode) may be taken as an initial microscopic control magnification level of the extended display mode. Meanwhile, the position information of the primary screen visual magnification region may inherit the position information of the microscopic region virtual box in the microscopic magnification mode or the position information of the primary screen visual magnification region in the synchronous replication mode.

A storage content, a storage form and a storage medium, and an initial parameter of the extended display mode are not limited in the present disclosure.

S202, scanning a state change of the zoomLevel and a movement state of the primary screen visual magnification region, recalculating the position information of the primary screen visual magnification region and synchronously updating the position information of the secondary screen visual magnification region when the state change or the movement state changes.

In some embodiments, the movement state of the primary screen visual magnification region is determined by scanning a change in the positions of the starting coordinates of the primary screen visual magnification region referred to the display image. For the state change of the zoomLevel, the dimensions of the primary screen visual magnification region may be adjusted according to a preset magnification strategy. For example, for a primary screen with a 16:9 display screen, the dimensions $(DispH_w, DispH_h)$ of the primary screen visual magnification region is calculated upon a step of zoomLevel+1 for each microscopic control magnification level as follows:

$$DispH_w = DispH_{w0} - 32 \times 2;$$

$$DispH_h = DispH_{h0} - 32 \times 2;$$

where $(DispH_{w0}, DispH_{h0})$ are the dimensions of the primary screen visual magnification region at the last zoomLevel. The position of the display image at an upper boundary is determined based on the starting coordinates and the dimensions of the primary screen visual magnification region, and accordingly the starting coordinates of the secondary screen visual magnification region are obtained, the dimensions of the secondary screen visual magnification region being the same as the dimensions of the primary screen, thereby obtaining the position information of the secondary screen visual magnification region after movement.

S203, obtaining image information within the primary screen visual magnification region and the secondary screen visual magnification region, respectively, and independently magnifying and displaying the image information within the primary screen visual magnification region and the secondary screen visual magnification region on a primary screen display region and a secondary screen display region, respectively, to achieve extended display.

In some embodiments, the processor may determine a second image feature based on the image content; determining a user operation habit, and obtaining a current operation feature; and determine a target mode based on the second image feature, the user operation habit, and the current operation feature.

The second image feature reflects a content distribution of the image content. In some embodiments, the second image feature may include a content type and position information. The content type may include a table, a text, an image, etc. The position information may be expressed as positions coordinates of the image content within the primary screen coordinate system.

For example, the second image feature may be represented as [(table, (x1, x2, y1, y2)), (text segment, (x3, x4, y3, y4))], where x1, x2, y1, and y2 represent a left boundary, a right boundary, an upper boundary, and a lower boundary of the table, respectively; x3, x4, y3, and y4 represent a left boundary, a right boundary, an upper boundary, and a lower boundary of the text segment, respectively.

In some embodiments, the processor may obtain the second image feature by recognizing the image content through an image recognition model. More descriptions regarding the image recognition model may be found in the present disclosure above.

The user operation habit refers to a user tendency to select different display modes. The user operation habit may be represented as an operation time and an operation frequency of the microscopic magnification mode, the extended display mode, and the synchronous replication mode. The operation time is duration that the user uses the display mode. The operation frequency is how often the user performs various operations in this display mode.

In some embodiments, the processor may determine the user operation habit in various ways. For example, the processor may determine the user operation habit by counting historical operation times and historical operation frequencies of the user various display modes.

The current operation feature is a feature parameter of a current user operation. For example, when the user performs a scrolling operation, the current operation feature includes a scrolling speed; when the user performs a zooming operation, the current operation feature includes a zooming frequency. The scrolling speed may be an average scrolling speed at which the user performs the scrolling operation. The processor may obtain an operation instruction of the user through a device such as a screen sensor or a mouse, and analyze to obtain the current operation feature of the user.

In some embodiments, the processor may determine the target mode based on the second image feature, the user operation habit, and the current operation feature through a mode determination model. The target mode may include one of the microscopic magnification mode, the extended display mode, and the synchronous replication mode.

The mode determination model is a model configured to determine the target mode. In some embodiments, the mode determination model may be a machine learning model.

In some embodiments, an input of the mode determination model may include the second image feature, the user operation habit, and the current operation feature, and an output of the mode determination model may include the target mode. The target mode is a display mode selected by the user, including one of the microscopic magnification mode, the extended display mode, and the synchronous replication mode.

In some embodiments, the mode determination model may be obtained by training based on a large number of second training samples with second labels. The second training samples may include a sample second image feature, a sample user operation habit, and a sample current operation feature, and the second labels may include a sample target mode.

In some embodiments, the second training samples may further include sample environmental data. More descriptions regarding the environmental data may be found in the present disclosure below.

In some embodiments, the second training samples may further include sample user eye movement data. More descriptions regarding the user eye movement data may be found in the present disclosure below.

In some embodiments, the processor may determine the second training samples with the second labels based on historical data. For example, the processor may obtain a plurality sets of historical data that the user uses any of the three display modes (e.g., the microscopic magnification mode, the extended display mode, and the synchronous replication mode) and a continuous use time exceeds a preset threshold as candidate data, filter a head and a tail of the continuous use time of each set of candidate data, randomly slice the filtered candidate data again, repeat the filtering and slicing operation for each set of candidate data to obtain a large number of candidate data fragments, and use each of the candidate data fragments as a second training sample, and determine a historical display mode corresponding to the second training sample as the second label.

In some embodiments, the content regarding obtaining the mode determination model by training an initial mode determination model based on the large number of second training samples with the second labels is similar to the content regarding obtaining the adjustment quantity prediction model by training the initial adjustment quantity prediction model based on the large number of first training samples with the first labels, which may be found in the present disclosure above.

In some embodiments, the processor may obtain the environmental data, and determine the target mode based on the environmental data, the second image feature, the user operation habit, and the current operation feature.

The environmental data reflects an environment in which the user is viewing the image content. In some embodiments, the environmental data may include an environmental brightness. The processor may obtain the ambient brightness through a light sensor or a camera.

In some embodiments, the input of the mode determination model may further include the environmental data, and the second training samples may further include the sample environmental data. More descriptions regarding the mode determination model may be found in present disclosure above.

By using the environmental data as the input of the mode determination model, the mode determination model can additionally consider the impact of the ambient light on the image content viewed by the user, which improves the accuracy of the model in predicting the target mode, and ensures that the content within the screen is always clear and visible.

In some embodiments, the processor may obtain the user eye movement data, and determine the target mode based on the user eye movement data, the environmental data, the second image feature, the user operation habit, and the current operation feature.

The user eye movement data is data related to a user eye movement. In some embodiments, the user eye movement data may include a blinking frequency, a gaze duration when the user gazes at the screen, or the like. The processor may obtain the user eye movement data through a device such as a camera.

In some embodiments, the input of the mode determination model may further include the user eye movement data, and the second training samples may further include the sample user eye movement data. More descriptions regarding the mode determination model may be found in the present disclosure above.

In some embodiments of the present disclosure, by using the eye movement data as the input of the mode determination model, it ensures that the mode determination model can consider the eye use and intent of the user, which helps to improve the accuracy of the model in predicting the target mode.

In some embodiments, the dual-screen assistive display method suitable for people with low vision may further include the synchronous replication mode S30.

FIG. 6 is a flowchart illustrating a synchronous replication mode in FIG. 1 according to some embodiments of the present disclosure. As shown in FIG. 6, the synchronous replication mode S30 may include operations S301-S303:

S301, determining position information of a primary screen visual magnification region on a display image based on a zoomLevel selected by a user, the position information including starting coordinates and dimensions of the primary screen visual magnification region. In some embodiments, a dual-screen assistive display device suitable for people with low vision may be configured to store and memorize the zoomLevel, including the zoomLevel familiar to the user or the zoomLevel at the time of last operation. According to the storage of the zoomLevel, when the user enters the synchronous replication mode, the zoomLevel of the last mode (e.g., the microscopic magnification mode or the extended display mode) may be taken as an initial microscopic control magnification level of the synchronous replication mode. Meanwhile, the position information of the primary screen visual magnification region may inherit the position information of the microscopic region virtual box in the microscopic magnification mode or the position information of the primary screen visual magnification region in the extended display mode, which is not limited in the present disclosure.

S302, scanning a state change of the zoomLevel and a movement state of the primary screen visual magnification region, recalculating the position information of the primary screen visual magnification region when the state change or the movement state changes.

S303, obtaining image information within the primary screen visual magnification region, and displaying the image information within the primary screen visual magnification region on a primary screen display region and a secondary screen display region, respectively, to achieve synchronous replication display.

Figure 7:
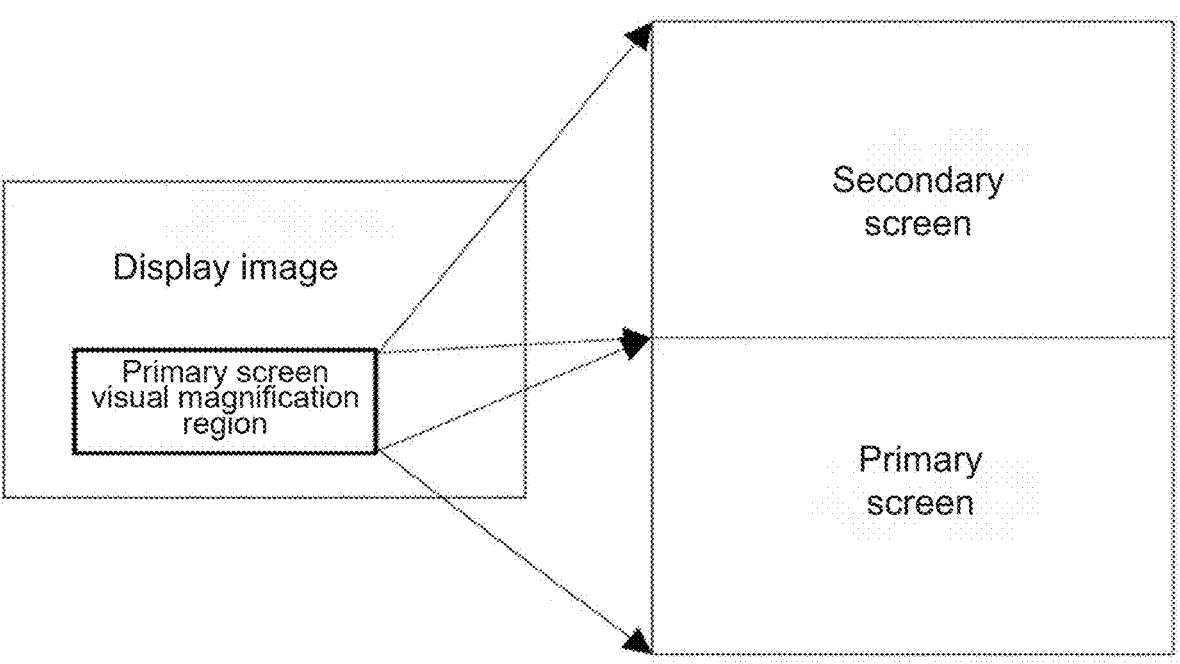
FIG. 7 is a schematic diagram illustrating a principle of the synchronous replication mode in FIG. 6 according to some embodiments of the present disclosure.

FIG. 7 is a schematic diagram illustrating a principle of the synchronous replication mode in FIG. 6 according to some embodiments of the present disclosure.

As shown in FIG. 7, the primary screen and the secondary screen may display the same image information, which facilitates multiple people to view the display image.

In some embodiments of the present disclosure, the synchronous replication mode enables dual-screen collaborative task allocation, thereby enhancing functional flexibility.

In some embodiments of the present disclosure, the dual-screen assistive display method suitable for people with low vision may arbitrarily switch among the microscopic magnification mode S10, the extended display mode S20, and the synchronous replication mode S30 for display, providing diverse display modes based on dual screens for people with low vision. In the extended display mode, the secondary screen displays an image in another FOV that is adjacent to the display image on the primary screen in the vertical direction or the horizontal direction, which increases the range of the readable image content at high magnification, and the FOV in the vertical direction or the horizontal direction is expanded by twice compared to the synchronous replication mode so as to enhance reading continuity.

Correspondingly, the present disclosure provides a dual-screen assistive display device suitable for people with low vision. The dual-screen assistive display device may comprise a position information determination unit 10, a position information mapping unit 20, a state scanning and updating unit 30, a position information reverse mapping unit 40, a content extraction unit 50, and a display control unit 60.

The position determination unit 10 refers to a module configured to determine position information of a microscopic region virtual frame.

In some embodiments, the position information determination unit 10 may be configured to determine the position information of the microscopic region virtual frame referenced to a display image on a primary screen based on a zoomLevel selected by a user, the zoomLevel being a current microscopic control magnification level, the position information including starting coordinates $(Zoom_x, Zoom_y)$ and dimensions $(Zoom_w, Zoom_h)$ of the microscopic region virtual frame.

The position information mapping unit 20 refers to a module that implements mapping of position information of a primary screen.

In some embodiments, the position information mapping unit 20 may be configured to map, based on a display parameter of the primary screen and a resolution $W_0 \times H_0$ of the display image on the primary screen, the position information of the microscopic region virtual frame to position information of a microscopic highlight frame within a primary screen coordinate system, the position information of the microscopic highlight frame including starting coordinates $(OSD_x, OSD_y)$ and dimensions $(OSD_w, OSD_h)$ of the microscopic highlight frame.

The state scanning and updating unit 30 is a module that scans a movement state of the microscopic highlight frame in real time.

In some embodiments, the state scanning and updating unit 30 may be configured to scan the movement state of the microscopic highlight frame within the primary screen coordinate system to obtain starting coordinates $(OSD_x', OSD_y')$ of the microscopic highlight frame after movement.

The position information reverse mapping unit 40 is a module that obtains the starting coordinates of the microscopic region virtual frame by mapping.

In some embodiments, the position information reverse mapping unit 40 may be configured to perform reverse mapping on the starting coordinates $(OSD_x', OSD_y')$ of the microscopic highlight frame after movement to obtain starting coordinates $(Zoom_x', Zoom_y')$ of the microscopic region virtual frame after movement.

The content extraction unit 50 is a functional module for extracting an image content.

In some embodiments, the content extraction unit 50 may be configured to extract the image content within the microscopic region virtual frame based on the dimensions $(Zoom_w, Zoom_h)$ and the starting coordinates $(Zoom_x', Zoom_y')$ of the microscopic region virtual frame after movement. The display control unit 60 may be configured to microscopically magnify an extracted image content within the microscopic region virtual frame on a secondary screen.

In some embodiments, the dual-screen assistive display device may magnify the display image using a two-stage magnification strategy based on a change in the zoomLevel selected by the user; when the zoomLevel ranges from 0 to $zoomLevel_{16R9}$, the dual-screen assistive display device may magnify the display image using a first magnification strategy to adapt to the size of the primary screen, the $zoomLevel_{16R9}$ being a magnification level at which the display image first adapts to the size of the primary screen; when the zoomLevel ranges from $zoomLevel_{16R9}$ to $zoomLevel_{max}$, the dual-screen assistive display device may proportionally magnify the display image adapted to the size of the primary screen using a second magnification strategy. More descriptions may be found in the present disclosure above.

According to the embodiments of the present disclosure, the device has the extended display mode, including: the position information determination unit 10 determining the position information of the primary screen visual magnification region on the display image based on the zoomLevel selected by the user; and determining the position information of the secondary screen visual magnification region adjacent to the primary screen visual magnification region in the horizontal direction or the vertical direction of the display image based on the boundary of the primary screen visual magnification region; the position information including the starting coordinates and the dimensions of the primary screen visual magnification region and the secondary screen visual magnification region, respectively; the state scanning and updating unit 30 scanning the state change of the zoomLevel and the movement state of the primary screen visual magnification region, recalculating the position information of the primary screen visual magnification region and synchronously updating the position information of the secondary screen visual magnification region when the state change or the movement state changes; the content extraction unit 50 obtaining the image information within the primary screen visual magnification region and the secondary screen visual magnification region, respectively; the display control unit 60 independently magnifying and displaying the image information within the primary screen visual magnification region and the secondary screen visual magnification region on the primary screen display region and the secondary screen display region, respectively, to achieve extended display.

According to the embodiments of the present disclosure, the device has the synchronous replication mode, including: the position information determination unit 10 determining the position information of the primary screen visual magnification region on the display image based on the zoomLevel selected by the user, the position information including the starting coordinates and the dimensions of the primary screen visual magnification region; the state scanning and updating unit 30 scanning the state change of the zoomLevel and the movement state of the primary screen visual magnification region, recalculating the position information of the primary screen visual magnification region when the state change or the movement state changes; the content extraction unit 50 obtaining the image information within the primary screen visual magnification region; the display control unit 60 displaying the image information within the primary screen visual magnification region on the primary screen display region and the secondary screen display region, respectively, to achieve synchronous replication display.

More descriptions regarding the specific method of the dual-screen assistive display device suitable for people with low vision may be found in the specific operations of the dual-screen assistive display method suitable for people with low vision, which are not repeated here. Various modules of the dual-screen assistive display device suitable for people with low vision may be implemented in whole or in part by software, hardware and combinations thereof. The above modules can be embedded in or independent of the processor in the computer apparatus in hardware form, or stored in the memory of the computer apparatus in software form so as to facilitate the processor to invoke and perform the operations corresponding to the above modules.

Figure 9:
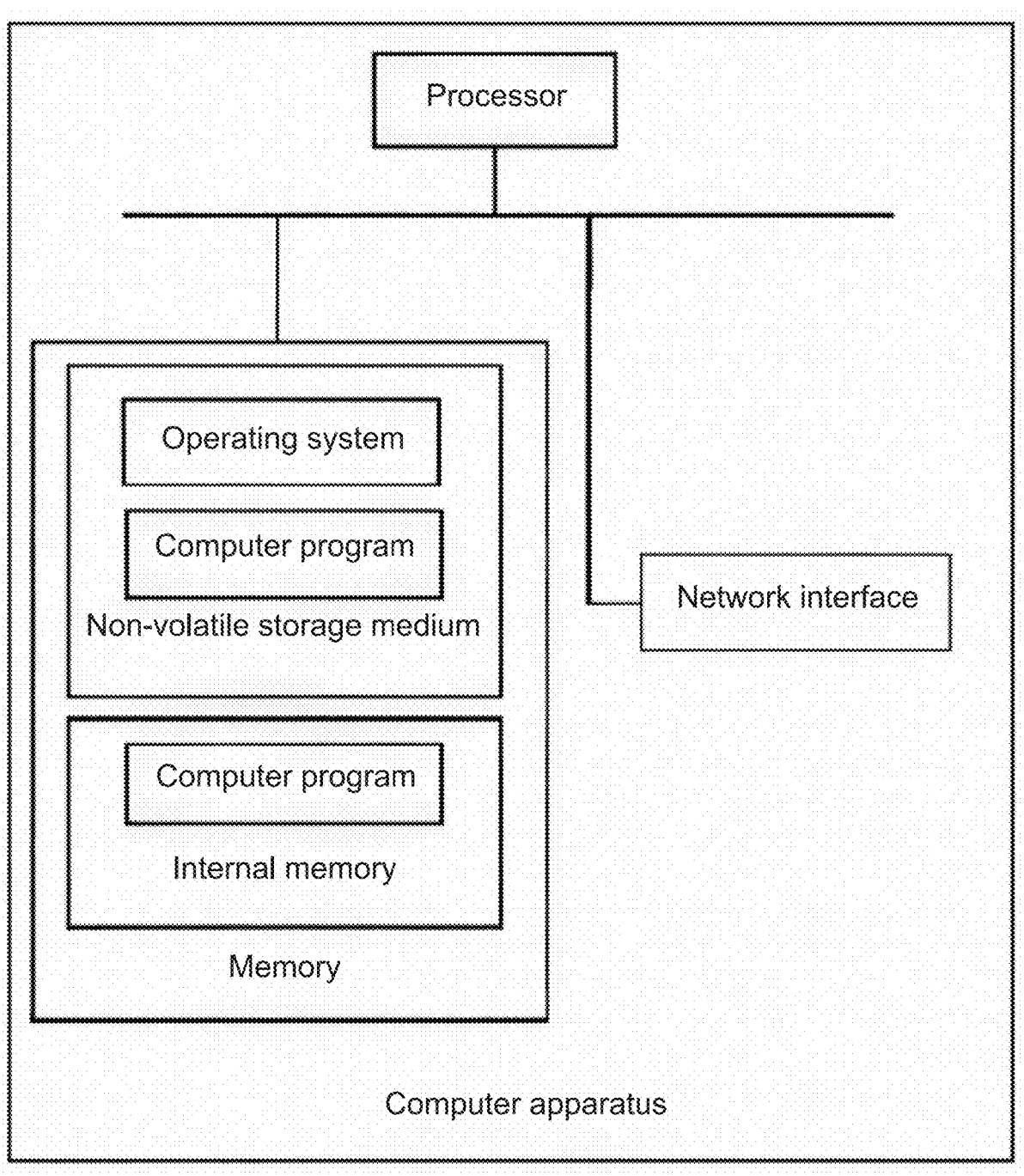
FIG. 9 is a schematic structural diagram illustrating a computer apparatus according to some embodiments of the present disclosure.

FIG. 9 is a schematic structural diagram illustrating a computer apparatus according to some embodiments of the present disclosure. The computer apparatus may comprise a processor, a memory, and a network interface which are connected via a system bus. The memory includes a non-volatile storage medium and an internal memory. The non-volatile storage medium of the computer apparatus stores an operating system, and may also store one or more computer programs that, when executed by the processor, direct the processor to implement the dual-screen assistive display method suitable for people with low vision. The internal memory may also store one or more computer programs that, when executed by the processor, direct the processor to implement the dual-screen assistive display method suitable for people with low vision.

It is understood by those skilled in the art that the structure illustrated in FIG. 9, which is merely a block diagram of a portion of the structure related to the present disclosure, does not constitute a limitation on the computer apparatus to which the present disclosure is applied, and the specific computer apparatus may include more or fewer components than shown in the drawings, or combine certain components, or have a different arrangement of components.

Figure 8:
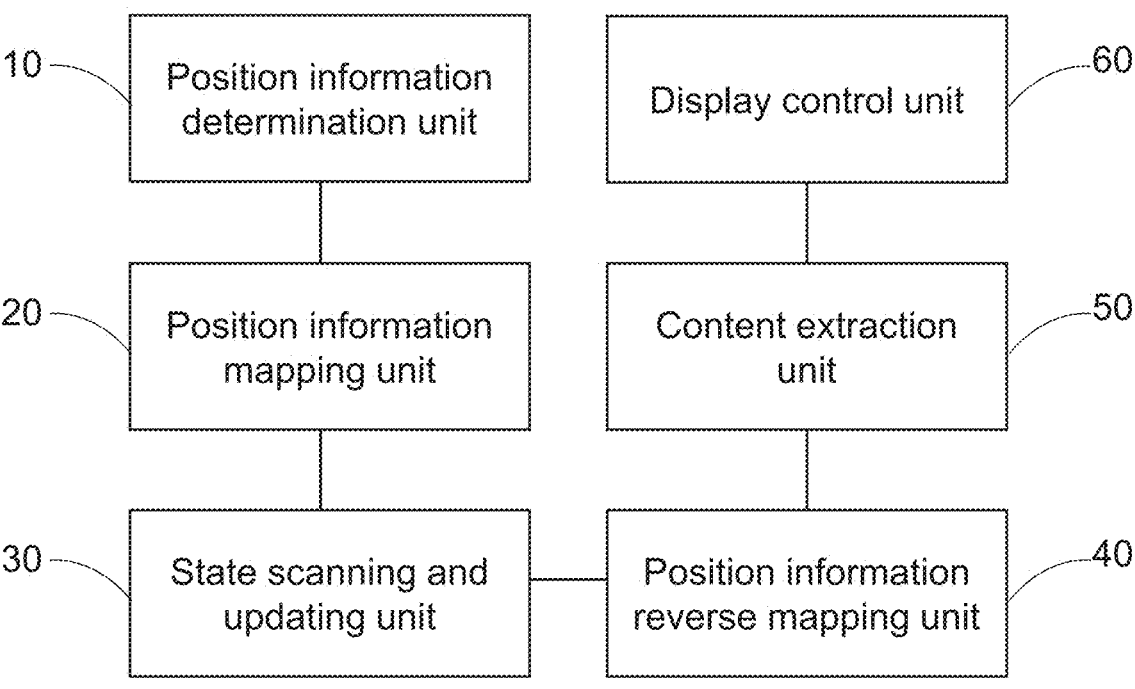
FIG. 8 is a schematic structural diagram illustrating a dual-screen assistive display device suitable for people with low vision according to some embodiments of the present disclosure.

In one embodiment, the dual-screen assistive display device for people with low vision provided by the present disclosure may be implemented in the form of a computer program, the computer program being operated on the computer apparatus as shown in FIG. 9. Program modules that constitute the dual-screen assistive display device suitable for people with low vision may be stored in the memory of the computer apparatus, such as the position information determination unit 10, the position information mapping unit 20, the state scanning and updating unit 30, the position information reverse mapping unit 40, and the display control unit 50 shown in FIG. 8. The computer programs composed of the program modules direct the processor to implement the operations of the dual-screen assistive display method for people with low vision in the embodiments of the present disclosure.

Although the present disclosure has been disclosed by the preferred embodiment, it is not intended to limit the present disclosure, and any person skilled in the art may make minor changes and modification without departing from the spirit and scope of the present disclosure. Therefore, the scope of protection of the present disclosure is subject to the scope of protection required by the claims.

What is claimed is:

1. A dual-screen assistive display method for people with less than half their vision, comprising:

determining position information of a microscopic region virtual frame referenced to a display image on a primary screen based on a zoomLevel selected by a user, wherein the zoomLevel is a current microscopic control magnification level, the position information includes starting coordinates ($Zoom_x$, $Zoom_y$) and dimensions ($Zoom_w$, $Zoom_h$) of the microscopic region virtual frame;

mapping, based on a display parameter of the primary screen and a resolution $W_0 \times H_0$ of the display image on the primary screen, the position information of the microscopic region virtual frame to position information of a microscopic highlight frame within a primary screen coordinate system, wherein the position information of the microscopic highlight frame includes starting coordinates ($OSD_x$, $OSD_y$) and dimensions ($OSD_w$, $OSD_h$) of the microscopic highlight frame;

scanning a movement state of the microscopic highlight frame within the primary screen coordinate system to obtain starting coordinates ($OSD_x'$, $OSD_y'$) of the microscopic highlight frame after movement;

performing reverse mapping on the starting coordinate ($OSD_x'$, $OSD_y'$) of the microscopic highlight frame after movement to obtain starting coordinates ($Zoom_x'$, $Zoom_y'$) of the microscopic region virtual frame after movement;

extracting an image content within the microscopic region virtual frame based on the dimensions ($Zoom_w$, $Zoom_h$) and the starting coordinates ($Zoom_x'$, $Zoom_y'$) of the microscopic region virtual frame after movement;

microscopically magnifying an extracted image content within the microscopic region virtual frame on a secondary screen;

wherein an aspect ratio of the primary screen is 16:9 and a resolution of the primary screen is $D_w \times D_h$; the display image is magnified using a two-stage magnification strategy based on a change in the zoomLevel selected by the user;

when the zoomLevel ranges from 0 to $zoomLevel_{16R9}$, the display image is magnified using a first magnification strategy to adapt to a size of the primary screen, wherein the $zoomLevel_{16R9}$ is a magnification level at which the display image first adapts to the size of the primary screen; when the zoomLevel ranges from $zoomLevel_{16R9}$ to $zoomLevel_{max}$, the display image adapted to the size of the primary screen is proportionally magnified using a second magnification strategy, wherein the $zoomLevel_{max}$ is a maximum magnification level;

the first magnification strategy includes:

when a condition $W_o \times D_h \geq H_o \times D_w$ is satisfied, the position information of the microscopic region virtual frame is expressed as:

$$Zoom_w = W_o - 2 \times 32 \times ZoomLevel;$$

$$Zoom_h = H_o;$$

$$Zoom_z = Zoom_{x0} - 32;$$

-continued $$Zoom_y = Zoom_{y0};$$

when a condition $W_o \times D_h < H_o \times D_w$ is satisfied, the position information of the microscopic region virtual frame is expressed as:

$$Zoom_w = W_o;$$

$$Zoom_h = H_o - 2 \times 32 \times ZoomLevel;$$

$$Zoom_z = Zoom_{x0};$$

$$Zoom_y = Zoom_{y0} - 32;$$

the second magnification strategy includes:
the position information of the microscopic region virtual frame is calculated upon a step of zoomLevel+1 for each microscopic control magnification level as follows:

$$Zoom_w = Zoom_{w0} - 32 \times 2;$$

$$Zoom_h = Zoom_{h0} - 32 \times 2;$$

$$Zoom_x = Zoom_{x0} - 32;$$

$$Zoom_y = Zoom_{y0} - 32;$$

where $(Zoom_{x0}, Zoom_{y0})$ and $(Zoom_{w0}, Zoom_{h0})$ are the starting coordinates and the dimensions of the microscopic region virtual frame before the change in the magnification level, $(Zoom_x, Zoom_y)$ and $(Zoom_w, Zoom_h)$ are the starting coordinates and the dimensions of the microscopic region virtual frame determined based on the zoomLevel; wherein W is a width of the display image, and H is a height of the display image.

2. The dual-screen assistive display method of claim 1, wherein the display parameter of the primary screen includes starting coordinates $(X_o, Y_o)$ and dimensions $(DW_o, DH_o)$ of a global visual region window that displays complete image information and outlines on the primary screen;

the position information of the microscopic region virtual frame is mapped to the position information of the microscopic highlight frame within the primary screen coordinate system using following equations:

$$OSD_w = Zoom_w \times DH_o \div W_o;$$
$$OSD_h = Zoom_h \times DH_o \div H_o;$$
$$OSD_x = X_o + Zoom_x \times DW_o \div W_o;$$
$$OSD_y = Y_o + Zoom_y \times DH_o \div H_o.$$

3. The dual-screen assistive display method of claim 1, wherein an adjustment range of the zoomLevel is in a range of 0-zoomLevel$_{max}$, wherein the zoomLevel$_{max}$ is related to the resolution of the display image and the resolution of the primary screen.

4. The dual-screen assistive display method of claim 1, wherein during scanning of the movement state of the microscopic highlight frame, whether the starting coordinates or endpoint coordinates of the microscopic highlight frame exceed the global visual region window is determined;

if the starting coordinates or the endpoint coordinates of the microscopic highlight frame exceed the global visual region window, the starting coordinates or the endpoint coordinates are clamped to boundary coordinates of the global visual region window to form position information of the microscopic highlight frame after movement.

5. The dual-screen assistive display method of claim 1, wherein after the image content within the microscopic region virtual frame is extracted, color modification is performed the image content based on a background color selected by the user before the image content is microscopically magnified on the secondary screen.

6. The dual-screen assistive display method of claim 1, further comprising an extended display mode, wherein the extended display mode includes:

determining position information of a primary screen visual magnification region on the display image based on the zoomLevel selected by the user, and determining position information of a secondary screen visual magnification region adjacent to the primary screen visual magnification region in a horizontal direction or a vertical direction of the display image based on a boundary of the primary screen visual magnification region, wherein the position information includes starting coordinates and dimensions of the primary screen visual magnification region and the secondary screen visual magnification region, respectively;

scanning a state change of the zoomLevel and a movement state of the primary screen visual magnification region, recalculating the position information of the primary screen visual magnification region and synchronously updating the position information of the secondary screen visual magnification region when the state change or the movement state changes;

obtaining image information within the primary screen visual magnification region and the secondary screen visual magnification region, respectively, and independently magnifying and displaying the image information within the primary screen visual magnification region and the secondary screen visual magnification region on a primary screen display region and a secondary screen display region, respectively, to achieve extended display.

7. The dual-screen assistive display method of claim 6, further comprising:

determining a second image feature based on the image content, the second image feature including a content type and the position information;

determining a user operation habit and obtaining a current operation feature, the current operation feature including one of a scrolling speed and a zooming frequency; and determining a target mode based on the second image feature, the user operation habit, and the current operation feature, the target mode including one of a microscopic magnification mode, the extended display mode, and a synchronous replication mode.

8. The dual-screen assistive display method of claim 7, wherein the determining a target mode based on the second image feature, the user operation habit, and the current operation feature comprises:

obtaining an environmental data and determining the target mode based on the environmental data, the second image feature, the user operation habit, and the current operation feature, the environmental data including an environmental brightness.

9. The dual-screen assistive display method of claim 8, further comprising:

obtaining user eye movement data, the user eye movement data including a blinking frequency and a gaze duration when the user gazes at a screen, the screen including the primary screen and the secondary screen; and determining the target mode based on the user eye movement data, the environmental data, the second image feature, the user operation habit, and the current operation feature.

10. The dual-screen assistive display method of claim 1, further comprising a synchronous replication mode, wherein the synchronous replication mode includes:

determining position information of a primary screen visual magnification region on the display image based on the zoomLevel selected by the user, wherein the position information includes starting coordinates and dimensions of the primary screen visual magnification region;

scanning a state change of the zoomLevel and a movement state of the primary screen visual magnification region, recalculating position information of the primary screen visual magnification region when the state change or the movement state changes;

obtaining image information within the primary screen visual magnification region and displaying the image information within the primary screen visual magnification region on a primary screen display region and a secondary screen display region to achieve synchronous replication display.

11. A computer apparatus, comprising a memory and a processor, the memory being configured to store one or more computer programs that, when executed by the processor, direct the processor to implement the method of claim 1.

12. The dual-screen assistive display method of claim 1, further comprising:

when the zoomLevel ranges from $zoomLevel_{16R9}$ to $zoomLevel_{max}$, using the first magnification strategy to proportionally magnify the display image adapted to the size of the primary screen;

determining a first image feature based on an image content of the display image, the first image feature including at least one of a text dense feature, an image texture feature, and an image color distribution; and determining a virtual frame adjustment quantity based on the first image feature.

13. The dual-screen assistive display method of claim 12, further comprising:

determining the virtual frame adjustment quantity based on the first image feature and a user eyestrain value, wherein the user eyestrain value is determined based on user eye movement data.

14. The dual-screen assistive display method of claim 12, further comprising:

determining weights of different content types in a second image feature based on the first image feature, wherein the second image feature reflects a content distribution of the image content; and determining the virtual frame adjustment quantity based on the weights of the different content types in the second image feature.

15. The dual-screen assistive display method of claim 12, wherein the determining a first image feature based on the image content of the display image comprises:

obtaining the first image feature by recognizing the image content through an image recognition model, the image recognition model being a machine learning model.

16. The dual-screen assistive display method of claim 12, wherein the determining a virtual frame adjustment quantity based on the first image feature comprises:

determining the virtual frame adjustment quantity based on the first image feature through an adjustment quantity prediction model, the adjustment quantity prediction model being a machine learning model.

17. The dual-screen assistive display method of claim 1, wherein the microscopically magnifying an extracted image content within the microscopic region virtual frame on a secondary screen comprises:

determining an edge enhancement intensity based on a user vision feature; and performing edge enhancement on the image content within the microscopic region virtual frame based on the edge enhancement intensity.

18. A dual-screen assistive display device-suitable for people with less than half their vision, comprising:

a position information determination unit configured to determine position information of a microscopic region virtual frame referenced to a display image on a primary screen based on zoomLevel selected by a user, wherein the zoomLevel is a current microscopic control magnification level, the position information includes starting coordinates ($Zoom_x$, $Zoom_y$) and dimensions ($Zoom_w$, $Zoom_h$) of the microscopic region virtual frame;

a position information mapping unit configured to map, based on a display parameter of the primary screen and a resolution $W_0 \times H_0$ of the display image on the primary screen, the position information of the microscopic region virtual frame to position information of a microscopic highlight frame within a primary screen coordinate system, wherein the position information of the microscopic highlight frame includes starting coordinates ($OSD_x$, $OSD_y$) and dimensions ($OSD_w$, $OSD_h$) of the microscopic highlight frame;

a state scanning and updating unit configured to scan a movement state of the microscopic highlight frame within the primary screen coordinate system to obtain starting coordinates ($OSD_x'$, $OSD_y'$) of the microscopic highlight frame after movement;

a position information reverse mapping unit configured to perform reverse mapping on the starting coordinates ($OSD_x'$, $OSD_y'$) of the microscopic highlight frame after movement to obtain starting coordinates ($Zoom_x'$, $Zoom_y'$) of the microscopic region virtual frame after movement;

a content extraction unit configured to extract an image content within the microscopic region virtual frame based on the dimensions ($Zoom_w$, $Zoom_h$) and the starting coordinates ($Zoom_x'$, $Zoom_y'$) of the microscopic region virtual frame after movement;

a display control unit configured to microscopically magnify an extracted image content within the microscopic region virtual frame on a secondary screen;

wherein an aspect ratio of the primary screen is 16:9 and a resolution of the primary screen is $D_w \times D_h$; the display image is magnified using a two-stage magnification strategy based on a change in the zoomLevel selected by the user; when the zoomLevel ranges from 0 to $zoomLevel_{16R9}$, the display image is magnified using a first magnification strategy to adapt to a size of the primary screen, wherein the $zoomLevel_{16R9}$ is a magnification level at which the display image first adapts to the size of the primary screen; when the zoomLevel ranges from zoomLevel$_{16R9}$ to zoomLevel$_{max}$;

the display image adapted to the size of the primary screen is proportionally magnified using a second magnification strategy, wherein the zoomLevel$_{max}$ is a maximum magnification level;

the first magnification strategy includes:

when a condition $W_o \times D_h \geq H_o \times D_w$ is satisfied, the position information of the microscopic region virtual frame is expressed as:

$$Zoom_w = W_o - 2 \times 32 \times ZoomLevel;$$

$$Zoom_h = H_o;$$

$$Zoom_x = Zoom_{x0} - 32;$$

$$Zoom_y = Zoom_{y0};$$

when a condition $W_o \times D_h < H_0 \times D_w$ is satisfied, the position information of the microscopic region virtual frame is expressed as:

$$Zoom_w = W_o;$$

$$Zoom_h = H_o - 2 \times 32 \times ZoomLevel;$$

$$Zoom_x = Zoom_{x0};$$

$$Zoom_y = Zoom_{y0} - 32;$$

the second magnification strategy includes: the position information of the microscopic region virtual frame is calculated upon a step of zoomLevel+1 for each microscopic control magnification level as follows:

$$Zoom_w = Zoom_{w0} - 32 \times 2;$$

$$Zoom_h = Zoom_{h0} - 32 \times 2;$$

$$Zoom_x = Zoom_{x0} - 32;$$

$$Zoom_y = Zoom_{y0} - 32;$$

where (Zoom$_{x0}$, Zoom$_{y0}$) and (Zoom$_{w0}$, Zoom$_{h0}$) are the starting coordinates and the dimensions of the microscopic region virtual frame before the change in the magnification level, (Zoom$_x$, Zoom$_y$) and (Zoom$_w$, Zoom$_h$) are the starting coordinates and the dimensions of the microscopic region virtual frame determined based on the zoomLevel; wherein W is a width of the display image, and H is a height of the display image.

19. The dual-screen assistive display device of claim 18, wherein the dual-screen assistive display device has an extended display mode, wherein the extended display mode includes:

the position information determination unit determining position information of a primary screen visual magnification region on the display image based on the zoomLevel selected by the user; and determining position information of a secondary screen visual magnification region adjacent to the primary screen visual magnification region in a horizontal direction or a vertical direction of the display image based on a boundary of the primary screen visual magnification region; wherein the position information includes starting coordinates and dimensions of the primary screen visual magnification region and the secondary screen visual magnification region, respectively;

the state scanning and updating unit scanning a state change of the zoomLevel and a movement state of the primary screen visual magnification region, recalculating the position information of the primary screen visual magnification region and synchronously updating the position information of the secondary screen visual magnification region when the state change or the movement state changes;

the content extraction unit obtaining image information within the primary screen visual magnification region and the secondary screen visual magnification region, respectively;

the display control unit independently magnifying and displaying the image information within the primary screen visual magnification region and the secondary screen visual magnification region on a primary screen display region and a secondary screen display region, respectively, to achieve extended display.

20. The dual-screen assistive display device of claim 18, wherein the device has a synchronous replication mode, wherein the synchronous replication mode includes:

the position information determination unit determining a position information of a primary screen visual magnification region on the display image based on the zoomLevel selected by the user, wherein the position information includes starting coordinates and dimensions of the primary screen visual magnification region;

the state scanning and updating unit scanning a state change of the zoomLevel and a movement state of the primary screen visual magnification region, recalculating position information of the primary screen visual magnification region when the state change or the movement state changes;

the content extraction unit obtaining image information within the primary screen visual magnification region; and the display control unit displaying the image information within the primary screen visual magnification region on a primary screen display region and a secondary screen display region, respectively to achieve synchronous replication display.

* * * * *